United States Patent [19]

Kampe et al.

[11] 4,285,946

[45] Aug. 25, 1981

[54] 4-AMINO-2-UREIDO (OR -THIOUREIDO)-PYRIMIDINE-5-CARBOXYLIC ACID ANILIDES

[75] Inventors: Klaus-Dieter Kampe, Bad Soden am Taunus; Ernold Granzer, Kelkheim, both of Fed. Rep. of Germany

[73] Assignee: Hoechst Aktiengesellschaft, Frankfurt am Main, Fed. Rep. of Germany

[21] Appl. No.: 101,160

[22] Filed: Dec. 7, 1979

[30] Foreign Application Priority Data

Dec. 9, 1978 [DE] Fed. Rep. of Germany ....... 2853220

[51] Int. Cl.³ ................ A61K 31/505; C07D 239/48; C07D 403/12
[52] U.S. Cl. ................................ 424/251; 544/122; 544/324; 544/325
[58] Field of Search ............ 544/324, 325, 122; 424/251

[56] References Cited

U.S. PATENT DOCUMENTS 3,325,496 6/1967 Critchley .................. 260/256.4
3,479,357 11/1969 Wagner .................... 260/256.4

*Primary Examiner*—Paul M. Coughlan, Jr.
*Attorney, Agent, or Firm*—Curtis, Morris & Safford

[57] ABSTRACT

What is disclosed are 4-amino-2-ureido (or -thioureido)-pyrimidine-5-carboxylic acid anilides of the formula

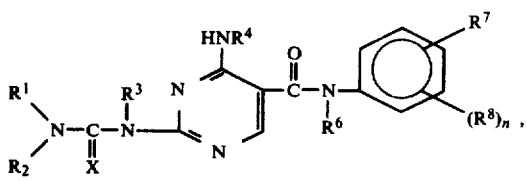

further defined in the specification, and physiologically acceptable acid addition salts thereof, methods for treating adiposity and disturbances of the lipometabolism with these compounds or salts, and pharmaceutical compositions containing these compounds or salts and useful for inducing anorexia or affecting the lipometabolism.

9 Claims, No Drawings

4-AMINO-2-UREIDO (OR -THIOUREIDO)-PYRIMIDINE-5-CARBOXYLIC ACID ANILIDES

4-Amino-2-ureido-(or -thioureido)-pyrimidine-5-carboxylic acid anilides of the general formula I

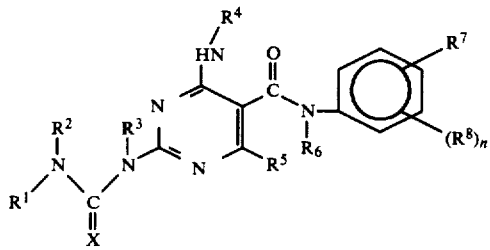

in which the substituents $R^1$ to $R^8$ and X and n have the indicated meanings, which, as such or in the form of their physiologically acceptable acid addition salts, possess valuable pharmacological properties, processes for their preparation, pharmaceutical preparations based on these compounds and their use as medicaments, especially in the treatment of adiposity and disturbances of the lipometabolism. The invention also relates to 2,4-diamino-pyrimidine-5-carbanilides of the general formula V

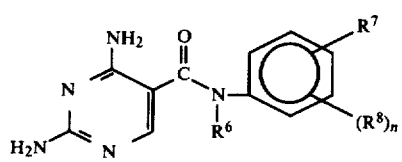

which can be used to prepare compounds of the formula I, and also processes for their preparation.

The invention relates to 4-amino-2-ureido-pyrimidne-5-carboxylic acid anilides, including their salts, processes for their preparation, medicaments containing these compounds and their use, especially in the treatment of disturbances of the lipometabolism and adiposity.

Virtually all of the anorectic agents available commercially are derivatives of β-phenylethylamine. Examples which may be mentioned here are phenmetrazine, amfepramone, norpseudoephedrine, fenfluramine and fenproporex. These preparations have the disadvantage that they exert more or less pronounced side effects on the central nervous system and/or the blood circulation [compare D. Craddock, Drugs 11, 378 (1976) and P. H. Connell, Side Effects of Drugs, volume 2, edited by M. N. G. Dukes, Excerpta Medica, Amsterdam 1978].

Recently an imidazo[2.1-a]isoindole derivative has been disclosed under the name mazindol as a newer preparation with an appetite-depressant action [J. H. Gogerty et al., Arch.int.Pharmacodyn. 214, 285 (1975)]. Although this compound is not a derivative of β-phenylethylamine, this anorectic agent is likewise not free from side effects on the central nervous system.

In several respects, the pharmacological spectrum of action is similar to that of amphetamine and related substances; like amphetamine, mazindol acts as a stimulant on the central nervous system by increasing the dopamine metabolism. The loss in effect which occasionally rapidly arises in the case of chronic administration is possibly due to a hyperinsulinaemia induced by mazindol. When treatment was carried out with mazindol, the typical side effects of appetite depressants which stimulate the central nervous system arose, such as sleeplessness, dizziness, obstipation, nervousness, tachycardia and extensive perspiration. Dryness of the mouth and a very pronounced antidepressant action are also observed. In the case of patients dependent on amphetamines, mazindol has a more amphetamine-like action than fenfluramine. [Compare Arznei-Telegramm 12/76, page 92; M. Babbini, M. Gaiardi and M. Bartoletti, Pharmacology 15, 46 (1977) and A. Kornhaber, Psychosomatics 14, 162 (1973)].

The object of the present invention is to provide a preparation which depresses the appetite and does not display these side effects and which, in particular, does not result in any undesired influence on the coronary circulation and central nervous systems.

It has now been found that 4-amino-2-ureido-(or -thioureido)-pyrimidine-5-carboxylic acid anilides of the general formula I

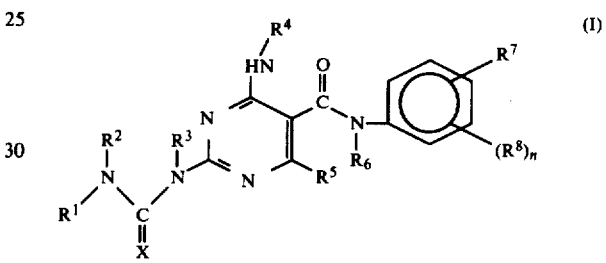

in which $R^1$ and $R^3$, which are identical or different, denote hydrogen, a $(C_1-C_3)$-alkyl group or a phenyl radical, $R^2$ denotes hydrogen, a $(C_1-C_{10})$-alkyl group, a $(C_3-C_4)$-alkenyl group, a $(C_4-C_8)$-cycloalkyl group, an aralkyl group with 1-2 C atoms in the alkyl part or a phenyl radical, it being possible for the aryl part of the aralkyl group or for the phenyl radical additionally to be substituted by 1-2 $(C_1-C_3)$-alkyl groups, 1-2 halogen atoms, 1-2 $(C_1-C_4)$-alkoxy groups, a trifluoromethyl group, a methoxycarbonyl or ethoxycarbonyl group and/or a methylenedioxy group, $R^4$ denotes hydrogen or a $(C_1-C_8)$-acyl group, $R^5$ denotes hydrogen, $R^6$ denotes hydrogen, a $(C_1-C_3)$-alkyl group, a $(C_3-C_4)$-alkenyl group, a benzyl group, which is optionally substituted in the phenyl radical by 1 or 2 chlorine atoms or 1 or 2 methoxy groups, or a phenyl radical, which is optionally substituted by 1 methyl group and/or 1 chlorine atom, $R^7$ denotes hydrogen, a $(C_1-C_3)$-alkyl group, a $(C_3-C_4)$-alkenyl group, a $(C_5-C_6)$-cycloalkyl group, a phenyl group, a halogen atom, or a trifluoromethyl, $(C_1-C_4)$-alkylthio, $(C_1-C_2)$-alkoxycarbonyl, cyano, acetamino, amino, nitro, carboxyl or $(C_1-C_4)$-alkoxy group or a radical

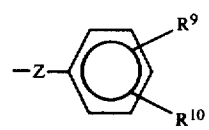

in which Z denotes an oxygen or sulfur atom or a

—CH$_2$— or —CH$_2$CH$_2$— group and R$^9$ and R$^{10}$, which are identical or different, denote a hydrogen, fluorine, chlorine or bromine atom, a (C$_1$-C$_3$)-alkyl group, a (C$_1$-C$_2$)-alkoxy group, an acetamino group or a (C$_1$14 C$_2$)-alkoxycarbonyl group or a carboxyl group, and R$^8$ denotes a fluorine, chlorine or bromine atom or a methyl, (C$_1$-C$_2$)-alkoxy or trifluoromethyl group, X denotes an oxygen or sulfur atom and n denotes 0, 1, 2 or 3, and the radicals R$^1$ and R$^2$ together also denote a branched or unbranched alkylene radical with 3-6 C atoms or denote the (—CH$_2$CH$_2$OCH$_2$CH$_2$—) radical and R$^2$ and R$^3$ together also denote a branched or unbranched alkylene radical with 2-8 C atoms, which, in addition, can be substituted by a (C$_2$-C$_4$)-alkenyl group or a phenyl radical, which is optionally substituted by a chlorine or bromine atom or a methyl, ethyl, methoxy or ethoxy group, or denote the (—CH=CH—) radical and, if n is 1, the radicals R$^7$ and R$^8$ together can also denote a methylenedioxy or ethylenedioxy group, and their physiologically acceptable acid addition salts possess valuable pharmacological properties. In particular, they have an anorectic action, that is to say they are able, by means of their appetite-depressant action, to prevent overweight, adiposity and the like. In addition, they are suitable for the treatment of disturbances of the lipometabolism.

The invention therefore relates to 4-amino-2-ureido-(or -thioureido)-pyrimidine-5-carboxylic acid anilides of the indicated formula I and their physiologically acceptable acid addition salts.

Preferred compounds of the general formula I are those in which the substituents have the following meanings:

R$^1$ is hydrogen, methyl or ethyl,

R$^2$ is hydrogen, a (C$_1$-C$_8$)-alkyl group, a (C$_3$-C$_4$)-alkenyl group, a (C$_5$-C$_6$)-cycloalkyl group or a benzyl or phenyl group, which optionally can additionally be substituted in the phenyl radical by a methyl group, 1 or 2 chlorine atoms, 1 or 2 methoxy groups, an ethoxy or trifluoromethyl group and/or a methylenedioxy group, R$^3$ is hydrogen or together with R$^2$ as indicated below, R$^4$ is hydrogen or acetyl, R$^6$ is hydrogen, a (C$_1$-C$_3$)-alkyl group, an allyl group or a benzyl group (optionally substituted by a chlorine atom), R$^7$ is a (C$_1$-C$_3$)-alkyl group, a phenyl group, a halogen atom, a CF$_3$, (C$_1$-C$_4$)-alkylthio, NO$_2$, (C$_1$14 C$_2$)-alkoxycarbonyl or (C$_1$-C$_4$)-alkoxy group or a radical

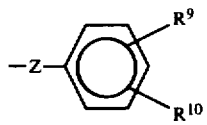

in which Z is a O or S atom and R$^9$ and R$^{10}$ are identical or different and denote a hydrogen, F, Cl or Br atom or a methyl or methoxy group and R$^8$ is methyl, fluorine, chlorine, bromine or a (C$_1$-C$_2$)-alkoxy or trifluoromethyl group, and n is 0, 1 or 2 and X is an oxygen atom and the radicals R$^1$ and R$^2$ together are also a tetra- or pentamethylene radical or the (—CH$_2$CH$_2$OCH$_2$CH$_2$—) radical or the radicals R$^2$ and R$^3$ together are also a branched or unbranched alkylene chain with 2-6 C atoms, which additionally can be substituted by a vinyl or phenyl group; and the actual alkylene chain, which together with the ureido group forms the ring, contains 2 C atoms, and if n=1, the radicals R$^7$ and R$^8$ together are also a methylenedioxy group in the 3,4-position.

Particularly preferred compounds of the general formula I are those in which the substituents have the following meanings:

R$^2$ is a (C$_1$-C$_8$)-alkyl group, an allyl or cyclohexyl group, a benzyl group, which is optionally substituted by a chlorine atom, or a phenyl radical, which is optionally substituted by 1 or 2 chlorine atoms or a methyl, trifluoromethyl or methoxy group, R$^3$ is hydrogen or together with R$^2$ as indicated below, R$^1$ is and R$^4$ hydrogen, R$^6$ is hydrogen or a methyl, ethyl, allyl or benzyl radical, R$^7$ is a (C$_1$-C$_3$)-alkyl group, a phenyl group, a fluorine, chlorine or bromine atom, a CF$_3$ or (C$_1$-C$_2$)-alkoxy group or a radical

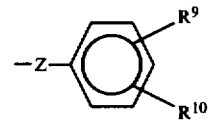

in which Z is a O or S atom and R$^9$ and R$^{10}$ are identical or different and denote a hydrogen or chlorine atom or a methyl or methoxy group, R$^8$ is methyl, fluorine, chlorine or a (C$_1$-C$_2$)-alkoxy or trifluoromethyl group and X is an oxygen atom and n=0, 1 or 2 and R$^2$ and R$^3$ together are also a branched or unbranched alkylene chain with 2-6 C atoms, which additionally can be substituted by a vinyl or phenyl group, and the actual alkylene chain, which together with the ureido group forms the ring, contains 2 C atoms, and, in addition, if n=1, R$^7$ and R$^8$ together are also a methylenedioxy group in the 3,4-position.

If more than one substituent R$^8$ is present, the meanings of the substituents are identical or different.

Suitable salts of the compounds, according to the invention, of the formula I are those with physiologically acceptable inorganic and organic acids, such as, for example, hydrochloric acid, hydrobromic acid or hydriodic acid, sulfuric acid, phosphoric acid, nitric acid, benzenesulfonic acid, toluenesulfonic acid, sulfamic acid, methylsulfuric acid, acetic acid, propionic acid, oleic acid, palmitic acid, stearic acid, malonic acid, maleic acid, succinic acid, glutaric acid, malic acid, tartaric acid, citric acid, fumaric acid, lactic acid, glycollic acid, pyruvic acid, benzoic acid, toluic acid, glutamic acid, furancarboxylic acid, salicylic acid or mandelic acid. Salts with physiologically acceptable inorganic acids or strongly acid derivatives to acid derivatives of medium strength of such acids are preferred.

The invention also relates to a process for the preparation of 4-amino-2-ureido(or -thioureido)-pyrimidine-5-carboxylic acid anilides of the general formula I, which comprises (a) reacting an isocyanate of the formula II a

         (II a)

in which $R^2$ has the abovementioned meanings in addition to hydrogen, with guanidine and then further reacting the reaction mixture, thus formed, with a compound of the formula III

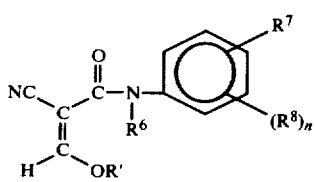         (III)

in which $R^6$, $R^7$ and $R^8$ and also n have the meanings indicated above under formula I and R' denotes a methyl or ethyl group, or (b) reacting compounds of the general formula IV

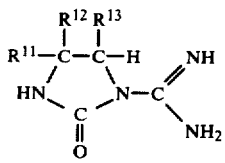         (IV)

in which $R^{11}$ denotes hydrogen, $(C_1-C_3)$-alkyl, $(C_2-C_4)$-alkenyl or phenyl, which is optionally substituted by a chlorine or bromine atom or a methyl, ethyl, methoxy or ethoxy group, and $R^{12}$ and $R^{13}$, which can be identical or different, each denote hydrogen or a $(C_1-C_3)$-alkyl group, or their acid addition salts, and, if salts of compounds of the formula IV are used, with the addition of a basic compound, with a compound of the formula III, in which $R^6$-$R^8$, R' and n have the meaning indicated above, with the formation of a compound of the general formula I in which X denotes O and $R^1$, $R^4$ and $R^5$ denote hydrogen and $R^2$ and $R^3$ together denote a

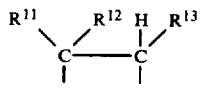

grouping, in which $R^{11}$-$R^{13}$ have the above meaning, and $R^6$, $R^7$ and $R^8$ and also n have the meaning indicated above, or (c) reacting an isocyanate of the formula II a or an isothiocyanate of the formula II b

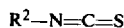         (II b)

in which $R^2$ has the meaning indicated above in addition to hydrogen, with a compound of the general formula V

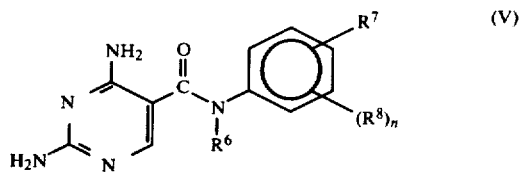         (V)

in which $R^6$, $R^7$ and $R^8$ and also n have the meanings indicated above under formula I, or (d) reacting a chloroformic acid amide or a chlorothioformic acid amide of the general formula VI

         (VI)

in which $R^1$ denotes a $(C_1-C_3)$-alkyl group or a phenyl radical, $R^2$ denotes a $(C_1-C_8)$-alkyl group, a $(C_3-C_4)$-alkenyl group, a $(C_5-C_6)$-cycloalkyl group or a benzyl or phenyl group, which optionally can be additionally substituted in the phenyl radical by a methyl group, 1 or 2 chlorine atoms, 1 or 2 methoxy groups or a methylenedioxy group, or $R^1$ and $R^2$ together denote a branched or unbranched alkylene radical with 3–6 C atoms or the ($-CH_2CH_2OCH_2CHHD$ 2—) radical, and X denotes an oxygen or sulfur atom, with a compound of the formula V in which $R^6$, $R^7$ and $R^8$ and also n have the meaning indicated above under formula I, or (e) reacting 4-amino-2-ureido-(or -2-thioureido)-pyrimidine-5-carboxylic acid anilides of the formula I, in which $R^4$ denotes hydrogen and $R^1$, $R^2$, $R^3$, $R^5$, $R^6$, $R^7$, $R^8$, X and n have the meanings indicated above under formula I, with an acylating agent of the formula VII

         (VII)

in which $R^{14}$ denotes a $(C_1-C_7)$-alkyl group, a cyclohexyl radical, a benzyl radical or a phenyl radical, which is optionally substituted by a methyl group, and Y denotes a chlorine or bromine atom or the group

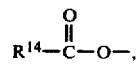

and optionally converting the compounds of the general formula I obtained by route (a)–(e) to their physiologically acceptable acid addition salts using organic or inorganic acids.

The reactions mentioned under (a) to (e) can be carried out in the presence or absence of a solvent or diluent.

The procedure indicated under (a) is advantageously carried out by reacting an isocyanate of the formula II a, appropriately with the additional use of a solvent, in amounts of 1.0–1.3 equivalents at a temperature of between $-50°$ C. and $+60°$ C., and in particular at between $-20°$ and $35°$ C., with 1 equivalent of guanidine and further reacting the resulting reaction mixture, without isolation of the guanylurea of the formula VIII formed and optionally with the use of further additional solvents, which can be different solvents, with a compound of the formula III at a temperature of between −20° C. and ±250° C.—preferably between +15° C. and +140° C. The compounds of the formula I thus formed ($R^1$, $R^3$, $R^4$ and $R^5$=H; $R^2$, $R^6$, $R^7$, $R^8$ and n with the above meaning) are usually obtained in crystalline form, or are obtained in crystalline form, and isolated, after evaporating off the solvents by conventional methods. Compounds of the formula III preferably used for this procedure are those in which $R^6$ denotes hydrogen and $R^7$, $R^8$ and $R'$ and also n have the meanings indicated above. The procedure indicated under (a) can be illustrated by the equation given below.

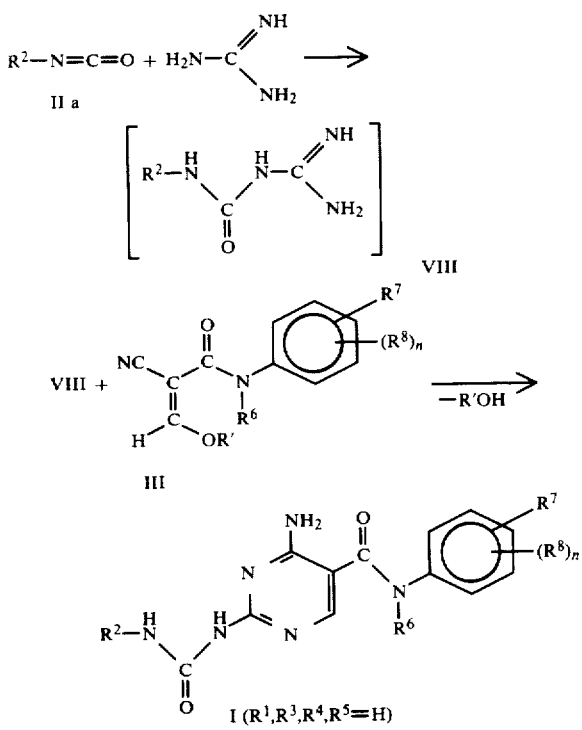

Solvents which can be used for this reaction are, for example, lower alkanols, such as methanol, ethanol, propanol, isopropanol, butanol, isobutanol, tert.-butanol and/or butanediol, ether, tetrahydrofuran, 1,2-dimethoxyethane, dioxan, acetonitrile, dimethylformamide, dimethylacetamide, sulfolane, sulfolene, chloroform, hexamethylphosphoric acid triamide, dimethylsulfoxide, diglycol dimethyl ether, methylene chloride or ethyl acetate. Suitable isocyanates, in addition to those named in the examples, are, for example, methyl isocyanate, ethyl isocyanate, isopropyl isocyanate, isobutyl isocyanate, pentyl isocyanate, hexyl isocyanate, 2-ethylhexyl isocyanate, decyl isocyanate, cyclopentyl isocyanate, cycloheptyl isocyanate, cyclooctyl isocyanate, allyl isocyanate, methallyl isocyanate, phenyl isocyanate, 4-methoxyphenyl isocyanate, 3,4-dimethoxy-phenyl isocyanate, 4-ethoxy-phenyl isocyanate, 4-butoxyphenyl isocyanate, o-, m- or p-toluyl isocyanate, 4-isopropyl-phenyl isocyanate, 4-fluoro-phenyl isocyanate, 3-ethoxycarbonylphenyl isocyanate or 3,4-methylenedioxy-phenyl isocyanate, benzyl isocyanate, 4-chlorobenzyl isocyanate, 4-methoxybenzyl isocyanate, 2-phenyl-ethyl isocyanate or 2-(3-methoxyphenyl)-ethyl isocyanate.

The isocyanates II a to be used as starting materials are in the main known compounds or can be prepared by known methods [in this context compare, for example, Liebigs Ann. d. Chem. 562, 75–136 (1949) and Houben-Weyl, Methoden d. Org. Chemie (Methods of Organic Chemistry), 4th edition, Volume VIII, Part 3, page 120, Stuttgart 1952].

The 3-alkoxy-2-cyano-acrylic acid anilides of the general formula III can be prepared from corresponding cyanoacetanilides by reaction with orthoformic acid esters in the presence of acetic anhydride and advantageously with the addition of Lewis acids as catalysts (in this context compare German Offenlegungsschrift No. 2,555,789).

The procedure indicated under (b) is advantageously carried out by reacting an amidino-imidazolidinone of the formula IV at a temperature of between −30° and +250° C.—preferably between +15° and +140° C.—and appropriately in the presence of a solvent, with a compound of the formula III. For this reaction, the compounds of the formula IV can be used in the form of the free bases or in the form of their acid addition salts. If salts are used, at least 1 equivalent or more of a basic compound is advantageously added. Preferably, the reaction of the salts of compounds of the formula IV with basic compounds is carried out at a temperature of between −30° and +50° before the other reactant, that is to say the compound of the formula III, is added. After a reaction time of a few minutes to several hours, the reaction with the compounds of the formula III can then be carried out in the same reaction vessel, without isolation of the amidino-imidazolidinones of the formula IV.

Basic compounds which can be used are, for example, alkali metal alkanolates or alkaline earth metal alkanolates of lower alkanols, alkali metal hydroxides, carbonates or bicarbonates, alkaline earth metal hydroxides, carbonates or bicarbonates, sodium hydride or tertiary amines, such as triethylamine or N,N-dimethylaniline.

Solvents which can be used are, for example, those which have been mentioned for the procedure indicated under (a).

The 1-amidino-imidazolidin-2-ones of the formula IV are preferably prepared by the process described in German Patent Application P 28 53 221.0. The process described in this Application comprises reacting 2-halogenoalkyl isocyanates of the formula $$\begin{array}{c} R^{12} \quad R^{13} \\ | \quad\quad | \\ R^{11}-C----C-H \\ | \quad\quad | \\ N \quad\quad Hal. \\ \| \\ C \\ \| \\ O \end{array}$$

in which Hal. denotes a chlorine, bromine or iodine atom and $R^{11}$, $R^{12}$ and $R^{13}$ have the meanings indicated under formula IV, with guanidine, optionally in the presence of a solvent or diluent.

Preferred compounds of the formula IV are those in which either the radicals $R^{11}$, $R^{12}$ and $R^{13}$ denote hydrogen or $R^{11}$ denotes a ($C_1$–$C_3$)-alkyl or alkenyl group or phenyl and $R^{12}$ denotes a methyl or ethyl group or hydrogen and $R^{13}$ denotes a methyl group or hydrogen, but $R^{12}$ represents hydrogen if $R^{13}$ denotes a methyl group.

It is not necessary to use the compounds of the formula IV or their acid addition salts in the pure crystalline form for carrying out the reaction. Instead of this, the crude products which are obtained from the preparation of these compounds and which sometimes are obtained in the form of oily products, can be employed.

The compounds of the general formula I which are formed frequently precipitate from the reaction medium in the form of virtually pure, crystalline substances, or they are isolated by conventional methods after evaporating off the solvents and, if necessary, purified by recrystallization or by chromatography.

The procedure indicated under (c) is advantageously carried out by reacting an isocyanate II a or isothiocyanate II b, with the additional use of a solvent and of a basic nitrogen compound which does not contain any N-H bonds, at a temperature of between 0° C. and 250° C.—preferably of between 40° C. and 150° C.—with a compound of the formula V. Preferably, this reaction is carried out with isocyanates II a.

Suitable solvents are, for example, in addition to the alcohols, those solvents which have been named for the procedure indicated under (a). Polar aprotic solvents, such as acetonitrile, N,N-dimethylformamide, dimethylsulfoxide, hexamethylphosphoric acid triamide, dioxan, dimethoxyethane, sulfolane, sulfolene, diglycol dimethyl ether (diglyme) or pyridine, are preferred.

It is also possible to use mixtures of the solvents listed and also mixtures of the solvents listed with other solvents.

The compounds of the formula V and the compounds of the formula I which are formed therefrom in accordance with the invention can be in the form of a suspension or solution in the particular solvent or diluent. The proportion of the dissolved substances is highly dependent on the dissolving power of the particular solvents and in general increases with increasing polarity of the solvents.

The basic nitrogen compounds which advantageously are additionally to be used as catalysts and which do not contain any NH grouping are to be understood as meaning nitrogen bases such as tertiary amines, completely alkyl-substituted amidines, including bicyclic representatives, and/or hetero-aromatic cyclic nitrogen compounds. Suitable tertiary amines are, for example, triethylamine or tributylamine, diethylcyclohexylamine, N-ethylpiperidine, N,N-dimethyl- or -diethyl-aniline or diaza-[2.2.2]bicyclooctane.

Suitable amidines are, for example, diazabicycloalkanes, such as, for example, the compound IX

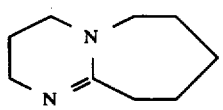
(IX)

and suitable hetero-aromatic cyclic nitrogen bases are, for example, pyridine, picoline, quinoline, quinaldine and/or N-methyl-imidazole.

These basic nitrogen compounds, which advantageously are additionally used as catalysts, are appropriately used in amounts of 0.01-2.00 and preferably 0.10-1.10 moles, based on 1 mole of a compound of the formula II a or II b.

The reaction between the compounds of the formula II a or b and the compounds of the formula V can, however, also be carried out without the addition of a basic nitrogen compound.

The ratios in which the isocyanates II a or isothiocyanates II b can be reacted with compounds of the formula V can vary greatly according to the invention and can be between 0.30 and 3.00 moles or more of a compound of the formula II a or b per mole of a compound of the formula V. Preferably, 0.90 to 1.60 moles of a compound of the formula II a or b are used per mole of a compound of the formula V.

The 2,4-diamino-pyrimidine-5-carbanilides of the general formula V are new compounds. The invention therefore also relates to compounds of the formula V and processes for their preparation. They are valuable intermediate products and are used, in particular, for the preparation of compounds of the formula I. In addition, they themselves display valuable pharmacological properties. They can be prepared by reacting guanidine or a guanidinium salt with a compound of the general formula III. This reaction is carried out analogously to the procedure indicated above under (a) or (b). The reaction conditions given in more detail above for this procedure thus likewise apply in the case of the preparation of the compounds of the formula V. If, for example, guanidinium salts are used, the reaction is appropriately carried out with the addition of a basic compound, as explained above under (a) and (b). The formation of the compounds of the formula V is illustrated by the equation given below.

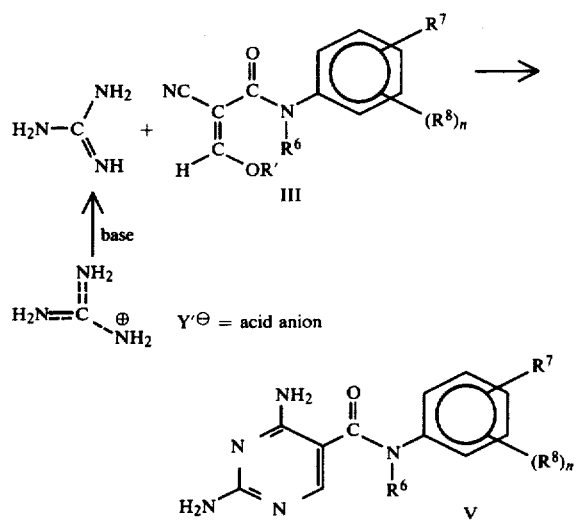

The notation chosen for formula III in respect of the E/Z isomerism is arbitrary. It is intended to include both forms. For the reaction described above and the procedures indicated under (a) and (b), the compounds of the formula III can be employed either in the pure E form or Z form or as mixtures of the E and Z forms. In every case, the particular pyrimidine derivatives according to the invention form, with cyclization.

The procedure indicated under (d) is advantageously carried out by allowing a chloroformic acid amide or chlorothioformic acid amide of the formula VI, in which $R^1$, $R^2$ and X have the meaning indicated above, to act, appropriately with the additional use of a solvent or diluent which is inert towards these compounds of the formula VI, in amounts of 1.0-1.8 equivalents, at a temperature of between 18° and 140° C.—preferably of between 40° and 100° C.—in the presence of, appropriately, 0.8-1.3 equivalents of a basic compound which is inert towards the compounds of the formula VI, on a compound of the formula V. Chloroformic acid amides of the formula VI, in which X denotes an oxygen atom, are preferably used for this reaction.

Suitable basic compounds, which advantageously are additionally used to bond the hydrogen chloride formed during the reaction, are, for example, those mentioned on page 17 in the explanation of the procedure indicated under (c). In principle, the reaction of the compounds of the formula VI with the compounds of the formula V can also be carried out without the addition of such a basic compound.

Suitable solvents and diluents are aprotic, preferably polar solvents, such as, for example, tetrahydrofuran, ether, 1,2-dimethoxyethane, dioxan, acetonitrile, sulfolane, chloroform, methylene chloride, 1,2-dichloroethane, ethyl acetate, acetone, dimethylsulfoxide or pyridine.

It is also possible to use mixtures of the solvents listed, and also mixtures of the solvents listed with other solvents.

The compounds of the formula V and also the compounds of the formula I formed therefrom by the action of chloroformic acid amides or chlorothioformic acid amides of the formula VI can be in the form of a suspension or solution in the particular solvent or diluent. The proportion of the dissolved substances is highly dependent on the dissolving power of the particular solvents and on the substituents in the phenyl radical of the anilide group of the compounds of the formula V or of the formula I. In general, the dissolving power in respect of the compounds of the formula V and I increases with the polarity of the solvents. Further details with regard to the way in which the procedure indicated under (d) is carried out can be taken from the examples. The chloroformic acid amides of the formula VI ($X=O$) are known in most cases or can be prepared by known methods [compare J. Chem. Soc. 1947, 307 and Houben-Weyl, Meth. d. Organ. Chem. (Methods of Organic Chemistry), Volume VIII, Part 3, page 117 (Stuttgart 1952)]. The synthesis of the chlorothioformic acid amides of the formula VI ($x=S$) has likewise been described in the chemical literature [compare Houben-Weyl, Meth. d. Organ. Chem. (Methods of Organic Chemistry) Volume IX, page 830 (Stuttgart 1955)].

The process indicated under (e) for the acylation of compounds of the formula I in which $R^4$ denotes hydrogen and the other radicals have the meaning indicated above is advantageously carried out by allowing an acylating agent of the formula VII to act on a compound of the formula I in which $R^4$ denotes hydrogen, optionally with the additional use of a solvent which is inert towards the acylating agent of the formula VII, at a temperature of between $-20$ and $160°$ C.—preferably of between $20°$ and $125°$ C. If acid chlorides or acid bromides are used as the acylating agents, a basic compound which is inert towards acid chlorides and acid bromides under the reaction conditions is then advantageously added—appropriately in an amount of at least one equivalent—and the reaction is preferably carried out in the presence of suitable solvents. Suitable basic compounds are the bases customarily to be used as acid-binding agents, such as, for example, tertiary amines, completely alkyl-substituted amidines (compare page 17), hetero-aromatic cyclic nitrogen bases, such as pyridine, picoline, quinoline, quinaldine and/or N-methylimidazole, and/or alkali metal carbonates and/or bicarbonates or alkaline earth metal carbonates and/or bicarbonates.

In principle, the acylation with acid chlorides or acid bromides can also be carried out without the addition of such a basic acid-binding agent.

The acid chlorides or acid bromides are employed in at least equivalent amounts or in excess.

If carboxylic acid anhydrides are used as the acylating agents, these are employed in at least equivalent amounts and preferably in excess, optionally with the additional use of suitable solvents. If the reaction is carried out without additional solvents, the carboxylic acid anhydrides are advantageously employed in excess, which can be, for example, 3 times to 30 times the molar amount, based on the compound of the formula I ($R^4=H$) to be acylated.

Suitable solvents optionally additionally to be used in the procedure indicated under (e) are all known solvents which are inert towards the acylating agents of the formula VII. Preferably, polar, aprotic solvents, such as, for example, acetonitrile, butyronitrile, tetrahydrofuran, 1,2-dimethoxyethane, dioxan, dimethylacetamide, methylene chloride, hexamethylphosphoric acid triamide, dimethylsulfoxide, sulfolane, chloroform or acetone, are used.

Of course, it is also possible to use mixtures of the solvents listed, and also mixtures of the solvents listed with other solvents.

The compounds of the formula I in which $R^4$ denotes hydrogen, and the acylation products formed therefrom, can be in the form of a suspension or solution in the particular solvent. Frequently, the major proportion of these compounds is in the form of a suspension. After the reaction has ended, the 4-acylamino-pyrimidine derivatives of the formula I ($R^4=$ acyl) which have formed are isolated as crystalline products by means of conventional methods and, if necessary, purified by recrystallization or chromatography.

Of course, when compounds of the general formula I are prepared, substituents in the phenyl radical of the anilide grouping of the compounds of the formula I can also be modified by known methods, that is to say converted to other substituents. Thus, for example, nitro groups can be converted to amino groups and these, in turn, can be converted to acylamino groups, or carboxyl groups can be converted to carboxylic acid ester groups and, vice versa, carboxylic acid ester groups can be converted to carboxyl groups.

In addition to the compounds described in the illustrative examples, it is also possible, according to the invention, to obtain, for example, the compounds of the general formula I listed in Table 1 which follows, and the acid addition salts of these compounds:

TABLE 1

(I)

[Structure (I): pyrimidine with HN-R⁴, C(=O)N(R⁶)-phenyl(R⁷)(R⁸)ₙ, R⁵, and N-R³-C(X)-N(R¹)(R²) substituents]

| | X | R¹ | R² | R³ | R⁴ | R⁵ | R⁶ | R⁷ | R⁸ | n |
|---|---|---|---|---|---|---|---|---|---|---|
| 1 | O | H | H | H | H | H | H | 3-CF₃ | — | 0 |
| 2 | O | H | H | H | H | H | CH₂C₆H₅ | H | — | 0 |
| 3 | O | H | H | H | H | H₃CCO | H | CH₂C₆H₅ | H | — | 0 |
| 4 | O | H | H | H | H | H | CH₂C₆H₅ | 4-Cl | — | 0 |
| 5 | O | H | H | H | H | H | CH₂C₆H₅ | 4-Cl | 3-Cl | 1 |
| 6 | O | H | H | H | H | H | CH₂C₆H₅ | 3-CF₃ | — | 0 |
| 7 | O | H | H | H | H | H | CH₂-(4-Cl-C₆H₄) | H | — | 0 |
| 8 | O | H | C₄H₉ | H | H | H | CH₃ | 4-Cl | 3-CF₃ | 1 |
| 9 | O | H | H | H | H | H | C₂H₅ | 3-CF₃ | 2-CH₃ | 1 |
| 10 | O | H | H | H | H | H | C₃H₅ | 3-OCH₃ | 4-OCH₃ | 1 |
| 11 | O | H | C₅H₁₁ | H | H | H | (H₃C)₂CH | 3-CF₃ | — | 0 |
| 12 | O | H | cyclohexyl | H | H | H | (H₃C)₂CH | 4-HC(CH₃)₂ | 3-Cl | 1 |
| 13 | O | H | C₃H₇ | H | H | H | C₆H₅ | 4-HC(CH₃)₂ | 3-Cl | 1 |
| 14 | O | H | C₆H₁₃ | H | H | H | C₆H₅ | 3-CF₃ | — | 0 |
| 15 | O | H | CH₃ | H | H | H | C₃H₅ | 4-O-C₆H₅ | 3-Cl, 6-CH₃ | 2 |
| 16 | O | H | C₆H₅ | H | H | H | CH₂-(4-OCH₃-C₆H₄) | 4-O-C₆H₅ | — | 0 |
| 17 | O | H | CH₃ | H | H | H | CH₂C₆H₅ | 3-CF₃ | — | 0 |
| 18 | O | H | CH₃ | H | H | H | CH(CH₃)₂ | 4-OC₂H₅ | 3-CF₃ | 1 |
| 19 | O | CH₃ | CH₃ | H | H | H | C₂H₅ | 4-Cl | 3-CF₃ | 1 |
| 20 | O | CH₃ | CH₃ | H | H | H | CH₂-(4-Cl-C₆H₄) | 4-HC(CH₃)₂ | 3-Cl | 1 |
| 21 | O | CH₃ | CH₃ | H | H | H | HC(CH₃)₂ | 4-O-C₆H₅ | 3-CF₃ | 1 |
| 22 | O | H | C₂H₅ | H | H | H | CH₂C₆H₅ | 4-Cl | 3-CF₃ | 1 |
| 23 | O | H | C₇H₁₅ | H | H | H | C₂H₅ | 3-OCH₃ | 4-OCH₃ | 1 |
| 24 | O | H | cyclohexyl | H | H | H | C₆H₅ | 3-CF₃ | — | 0 |
| 25 | O | H | H₃C-C(C₃H₇)(CH₃)-CH₂— | H | H | H | H | 2-OCH₃ | 5-CF₃ | 1 |
| 26 | O | H | " | H | H | H | H | 4-S-(4-Cl-C₆H₄) | 3-CF₃ | 1 |
| 27 | O | H | " | H | H | H | H | 4-SCH₃ | 3-CF₃ | 1 |
| 28 | O | H | (H₃C)₂C-CH₂— | H | H | H | H | 2-OC₆H₅ | 5-CF₃ | 1 |
| 29 | O | H | " | H | H | H | H | 4-SCH₃ | 3-CF₃ | 1 |
| 30 | O | H | " | H | H | H | H | 4-O-(3-C₃H₇, 4-CH₃-C₆H₃) | 3-CF₃ | 1 |
| 31 | O | H | " | H | H | H | H | 4-O-(4-Cl-C₆H₄) | 3-CF₃ | 1 |
| 32 | O | H | " | H | H | H | H | 4-O-(4-OCH₃-C₆H₄) | 3-CF₃ | 1 |
| 33 | O | H | " | H | H | H | H | 2-S-(4-Cl-C₆H₄) | 5-CF₃ | 1 |

TABLE 1-continued (I)

| | X | $R^1$ | $R^2$ | $R^3$ | $R^4$ | $R^5$ | $R^6$ | $R^7$ | $R^8$ | n |
|---|---|---|---|---|---|---|---|---|---|---|
| 34 | O | H | " | | H | H | H | 2-O-C$_6$H$_4$-OCH$_3$ | 5-CF$_3$ | 1 |
| 35 | O | H | " | | H | H | H | 4-OC$_4$H$_9$ | 3-CF$_3$ | 1 |
| 36 | O | H | " | | H | H | H | 4-S-C$_6$H$_4$-Cl | 3-CF$_3$ | 1 |
| 37 | O | H | " | | H | H | H | 4-S-C$_6$H$_4$-CH$_3$ | 3-CF$_3$ | 1 |
| 38 | O | H | " | | H | H | H | 4-S-C$_6$H$_4$-CH(CH$_3$)$_2$ | 3-CF$_3$ | 1 |
| 39 | O | H | " | | H | H | H | 2-SC$_4$H$_9$ | 5-CF$_3$ | 1 |
| 40 | O | H | " | | H | H | H | 4-SC$_2$H$_5$ | 3-CF$_3$ | 1 |
| 41 | O | H | " | | H | H | CH$_2$C$_6$H$_5$ | 4-OC$_6$H$_5$ | 3-CF$_3$ | 1 |
| 42 | O | H | " | | H | H | H | 4-O-C$_6$H$_4$-C$_2$H$_5$ | 3-CF$_3$ | 1 |
| 43 | O | H | (H$_5$C$_2$)$_2$CH—CH$_2$— | | H | H | H | 5-CF$_3$ | 2-Cl | 1 |
| 44 | O | H | H$_5$C$_2$—CH(H)—CH(H)—C$_2$H$_5$ | | H | H | H | 3-CF$_3$ | — | 0 |
| 45 | O | H | (CH$_3$)(H$_5$C$_2$)C(CH$_2$—) | | H | H | H | 5-CF$_3$ | 2-F | 1 |
| 46 | O | H | (CH$_3$)(H$_9$C$_4$)C(CH$_2$—) | | H | H | H | 3-CF$_3$ | — | 0 |
| 47 | O | H | (CH$_3$)(H$_7$C$_3$)C(CH$_2$—) | | H | H | CH$_2$-C$_6$H$_4$-Cl | 3-CF$_3$ | — | 0 |
| 48 | O | H | (H$_3$C)$_2$CH—CH$_2$— | | H | H | CH$_3$ | 3-CF$_3$ | 4-Cl | 1 |
| 49 | O | H | " | | H$_5$C$_6$—CH$_2$—CO | H | H | 3-CF$_3$ | — | 0 |
| 50 | O | H | C$_4$H$_9$ | H | H$_7$C$_3$CO | H | H | 4-OC$_2$H$_5$ | 3-Cl | 1 |
| 51 | S | CH$_3$ | CH$_3$ | H | H | H | H | 3-CF$_3$ | — | 0 |
| 52 | S | CH$_3$ | CH$_3$ | H | H | H | H | 4-OC$_6$H$_5$ | 2-Cl | 1 |
| 53 | S | H | C$_6$H$_5$ | H | H | H | H | 3-Cl | 2-CH$_3$ | 1 |
| 54 | S | H | C$_3$H$_5$ | H | H | H | CH$_2$C$_6$H$_5$ | 4-Cl | — | 0 |
| 55 | S | H | CH$_3$O-C$_6$H$_4$- | H | H | H | H | 4-OC$_6$H$_5$ | — | 0 |
| 56 | S | H | C$_3$H$_5$— | H | H | H | CH$_3$ | 4-SCH$_3$ | 3-Cl | 1 |
| 57 | O | H | (H$_3$C)$_2$CH—CH$_2$— | | H | H | CH$_2$CH=CH$_2$ | 3-CF$_3$ | 6-F | 1 |
| 58 | O | H | " | | H | H | H | 2-O-C$_6$H$_4$-CH$_3$ | 5-CF$_3$ | 1 |
| 59 | O | H | —H$_2$C—CH$_2$— | | H | H | CH$_2$C$_6$H$_5$ | 4-NH$_2$ | — | 0 |
| 60 | O | H | " | | H | H | H | 4-OC$_6$H$_5$ | 3-CF$_3$ | 1 |
| 61 | O | H | H$_3$C—C(C$_3$H$_7$)(CH$_2$—) | | H | H | H | 4-CF$_3$ | 2-F | 1 |
| 62 | O | H | " | | H | H | H | 4-O-C$_6$H$_4$-OCH$_3$ | 3-CF$_3$ | 1 |
| 63 | O | H | " | | H | H | H | 2-OC$_6$H$_5$ | 5-CF$_3$ | 1 |

TABLE 1-continued (I)

| | X | R¹ | R² | R³ | R⁴ | R⁵ | R⁶ | R⁷ | R⁸ | n |
|---|---|---|---|---|---|---|---|---|---|---|
| 64 | O | —(CH₂)₅— | | H | H | H | H | 4-OC₆H₅ | — | 0 |
| 65 | O | " | | H | H | H | H | 3-CF₃ | — | 0 |
| 66 | O | " | | H | H | H | H | | 3,4-O—CH₂—O— | 1 |
| 67 | O | —CH₂CH₂OCH₂CH₂— | | H | H | H | H | | 3,4-O—CH₂—O— | 1 |
| 68 | O | " | | H | H | H | CH₂C₆H₅ | H | — | 0 |
| 69 | O | —(CH₂)₄— | | H | CH₃CO | H | H | 4-CH₃ | 3-Cl | 1 |
| 70 | S | " | | H | H | H | H | 3-CF₃ | — | 0 |
| 71 | S | —(CH₂)₅— | | H | H | H | CH₂C₆H₅ | H | — | 0 |
| 72 | O | H | (H₃C)₂CH—CH₂— | H | H | H | CH₂C₆H₅ | 3-CF₃ | — | 0 |
| 73 | O | H | H₅C₆—CH(H)—CH₂— | H | H | H | H | 4-COOC₂H₅ | — | 0 |
| 74 | O | H | " | H | H | H | CH₃ | 3-CF₃ | — | 0 |
| 75 | O | H | H₃CO-C₆H₄-C(CH₃)—CH₂— | H | H | H | H | 3-CF₃ | — | 0 |
| 76 | O | H | H₅C₆—C(CH₃)₂—CH₂— | H | H | H | H | 3-CF₃ | — | 0 |
| 77 | O | H | " | H | H | H | H | 3-CF₃ | 5-CH₃ | 1 |
| 78 | O | H | (H₃C)₂C(CH₂—)—CH₂— | H | H | H | H | 5-CF₃ | 2-Br | 1 |
| 79 | O | H | " | H | H | H | H | 3-CF₃ | 4-F | 1 |
| 80 | O | H | " | H | H | H | H | 5-CF₃ | 2-SCH₃ | 1 |
| 81 | O | H | " | H | H | H | H | 3-CF₃ | 4-CH₃ | 1 |
| 82 | O | H | " | H | H | H | H | 3-CF₃ | 2-Cl | 1 |
| 83 | O | H | " | H | H | H | H | 3-CF₃ | 2-F | 1 |
| 84 | O | H | " | H | H | H | H | 3-CF₃ | 5-F | 1 |
| 85 | O | H | " | H | H | H | H | 3-CF₃ | 5-Cl | 1 |
| 86 | O | H | " | H | H | H | H | 3-CF₃ | 5-CH₃ | 1 |
| 87 | O | H | " | H | H | H | H | 5-CF₃ | 2-CH₃ | 1 |
| 88 | O | H | " | H | H | H | H | 3-CF₃ | 4-Br | 1 |
| 89 | O | H | " | H | H | H | H | 3-CF₃ | 4-OCH₃ | 1 |
| 90 | O | H | " | H | H | H | H | 3-CF₃ | 5-OCH₃ | 1 |
| 91 | O | H | " | H | H | H | H | 5-CF₃ | 2-OCH₃ | 1 |
| 92 | O | H | " | H | H | H | H | 2-OC(CH₃)₃ | 5-CF₃ | 1 |
| 93 | O | H | " | H | H | H | H | 3-CF₃ | 4-OC₂H₅ | 1 |
| 94 | O | H | " | H | H | H | H | 5-CF₃ | 2-OC₂H₅ | 1 |
| 95 | O | H | " | H | H | H | H | 2-O-C₆H₄-Cl | 5-CF₃ | 1 |
| 96 | O | H | " | H | H | H | H | 2-O-C₆H₄-OCH₃ | 5-CF₃ | 1 |
| 97 | O | H | " | H | H | H | H | 4-OC(CH₃)₃ | 3-CF₃ | 1 |
| 98 | O | H | " | H | H | H | H | 2-S—C₆H₅ | 5-CF₃ | 1 |
| 99 | O | H | " | H | H | H | H | 4-O-C₆H₄-CH₃ | 3-CF₃ | 1 |
| 100 | O | H | " | H | H | H | H | 4-O-C₆H₄-OC₂H₅ | 3-CF₃ | 1 |
| 101 | O | H | " | H | H | H | H | 4-O-C₆H₄-OC₂H₅ | 3-CF₃ | 1 |

TABLE 1-continued

| X | R¹ | R² | R³ | R⁴ | R⁵ | R⁶ | R⁷ | R⁸ | n |
|---|----|----|----|----|----|----|----|----|---|
| 102 | O | H | " | H | H | H | 2-O—⟨◯⟩—OC₂H₅ | 5-CF₃ | 1 |

The new compounds, according to the invention, of the general formula I possess valuable pharmacological properties and can therefore be used as medicaments. They are distinguished, for example, by advantageous actions on the lipometabolism and they are particularly suitable as anorectic agents. In contrast to the β-phenylethylamine analogs and derivatives and compounds of the mazindol type mentioned initially, they are distinguished by the lack of undesired side effects on the coronary circulation system and by the lack of stimulating effects on the central nervous system and are therefore superior to these compounds. Since overweight is very frequently associated with disturbances of the purine metabolism (increases in serum uric acid) or hyperlipidaemia, additional antagonistic properties against these disfunctions of the metabolism are desirable and of particular advantage. Individual representatives of the formula I also display these advantageous hypouricaemic properties.

The new compounds of the general formula V, which are intermediate products for the synthesis of the compounds I, and also their acid addition salts, themselves also have anorectic actions of varying intensity. These compounds also exert, in addition, an advantageous action on the lipometabolism and the purine metabolism. The 2,4-diaminopyrimidine-5-carbanilides of the formula V have a hypouricaemic action. In addition, antiphlogistic properties have also been observed.

The appetite-inhibiting action of the new compounds of the formula I manifests itself in a pharmacological test on peroral and/or intraperitoneal administration to fasting rats in an inhibition of the feed intake, and on semichronic administration results in a suppression of the increase in body weight.

The test to determine the anorectic action (inhibition of feed consumption) of the compounds in an acute test on rats was carried out by measuring the feed consumption of rats, which had been fasting for 48 hours, over a period of 6 hours at hourly intervals. The rats used were male rats of the Wistar strain with a body weight of more than 110 g, which had been acclimatized in the test rooms for several days. They had free access to feed and water up to the start of the test. The feed was withdrawn from the rats 48 hours before the substance was administered. The substance to be tested was then administered to the rats, either orally (using a probang) or intraperitoneally in 1% strength Tylose in a volume of 0.5 ml/100 g of body weight. Half an hour after the intraperitoneal administration or 1 hour after the oral administration, the animals were offered an accurately measured amount of pelleted feed and the amount of feed eaten was determined hourly over a period of 6 hours, by back-weighing the amount of feed offered. As a rule, 6 rats were used per compound and per dosage and during the test period the rats were kept individually in type 3 Makrolon cages.

During the determination of the feed consumption, the average value for the group at any time was calculated from the feed consumption of each individual animal. This average value for the feed consumption was compared with that for a control group, tested at the same time, which had received only the solvent or suspending agent. The changes compared with the control group are given in % in Tables I and II below.

TABLE I

| Compound according to Example | Dose mg/kg | % feed consumption compared with control group after | | | | | |
|---|---|---|---|---|---|---|---|
| | | 1 | 2 | 3 | 4 | 5 | 6 |
| | | hours | | | | | |
| 3 | 0.3 | −35 | −25 | −13 | −10 | − 6 | −15 |
|   | 0.1 | −27 | −13 | − 9 | −11 | −12 | −14 |
| 23 | 1 | −26 | −25 | −43 | −28 | −24 | −22 |
| 15 | 3 | −70 | −49 | −38 | −28 | −21 | −26 |
|   | 1 | + 5 | − 4 | −26 | −28 | −19 | −16 |
| 1 | 10 | −37 | −37 | −30 | −40 | −43 | −35 |

Inhibition of the feed intake (in %, compared with a control group) by rats, which have been fasting for 48 hours, over a period of 1 to 6 hours. Intraperitoneal administration ½ hour before feed is offered.

TABLE II

| Compound according to Example | Dose mg/kg | % feed consumption compared with control group after | | | | | |
|---|---|---|---|---|---|---|---|
| | | 1 | 2 | 3 | 4 | 5 | 6 |
| | | hours | | | | | |
| 3 | 10 | −27 | −13 | −15 | −17 | −10 | −11 |
|   | 3 | −26 | − 8 | −15 | −16 | − 9 | −10 |
| 23 | 3 | −49 | −17 | −24 | −28 | −12 | −10 |
| 15 | 3 | −12 | − 6 | −27 | −21 | −14 | −14 |
| 1 | 10 | −74 | −49 | −47 | −47 | −39 | −36 |

Inhibition of the feed intake (in %, compared with a control group) by rats, which have been fasting for 48 hours, over a period of 1 to 6 hours. Peroral administration 1 hour before feed is offered.

The advantageous effect on the lipometabolism in the sense of a hypolipidaemic and/or hypouricaemic action manifests itself in rats which are treated orally for several days with the compounds mentioned and from which blood has been taken before and after the treatment. In the serum obtained therefrom, enzymatic determinations of cholesterol, by the CHOD-PAP method (Boehringer), triglycerides, by the Eggstein and Kreutz method, and uric acid, by the M. Kortüm and O. Kling method (Arztl. Lab. 18, 33 (1972)) are carried out and the changes are compared with the initial value or with a control group which is tested at the same time and is treated only with the solvent or suspending agent.

In further investigations relating to the influence of compounds according to the invention on the lipometabolism it was observed that these compounds greatly reduce the concentration of the etherogenic lipoprotein fractions LDL and VLDL in the serum, while they have no influence on the protective factor HDL, or reduce this to only a very slight extent. Accordingly, the ratio of HDL to the etherogenic fractions is increased severalfold (based on an untreated control group). In contrast, clofibrate, which is a known agent for lowering the lipid level, lowers the HDL-cholestrol to a considerably greater extent than the LDL- and VLDL-cholesterol. Also, benzafibrate, which is a clofibrate analog, lowers HDL-cholesterol to virtually the same extent as LDL-cholesterol. In addition, clofibrate HDL using a preparative ultracentrifuge (Beckman L 250 B, Rotor FW 50 Ti).

A test combination from BOEHRINGER/Mannheim was used for the enzymatic determination of the cholesterol by the CHOD-PAP method (RÖSCHLAU, P., BERNDT, E. and W. GRUBER: 9th int. Congr. on clin. Chemistry, Toronto, 1975, Abstract No. 1) and of the triglycerides (EGGSTEIN, M. and KREUTZ, F. H.: Klin. Wschr. 44, 262 and 267 (1966); WAHLEFELD, A. W., in H. O. BERGMEIER: Methoden der enzymatischen Analyse (Methods of Enzymatic Analysis), 3rd edition, Volume II, Verlag Chemie 1974, page 1878) in the separated lipoprotein fractions, and the protein was determined by the method of LOWRY et al. (LOWRY, O. H., ROSEBOROUGH, N. J., FARR, A. L. and R. J. RANDELL: J. Biol. Chem. 193, 265 (1951)).

TABLE III

| Compound | Dose mg/kg/ day | Number of animals | CHOLESTEROL in VLDL | CHOLESTEROL in LDL | CHOLESTEROL in HDL | PROTEIN in VLDL | PROTEIN in LDL | PROTEIN in HDL | HDL VLDL + LDL Cholesterol | HDL VLDL + LDL Protein | Relative liver weight | Body weight | Feed consumption |
|---|---|---|---|---|---|---|---|---|---|---|---|---|---|
| according to Example 1 | 30 | 10 | −100 | −80 | −14 | −40 | −39 | +1 | 580 | 150 | −5 | −6 | −10 |
|  | 20 | 10 | −87 | −56 | −25 | −43 | −30 | +7 | 200 | 170 | −5 | −9 | −21 |
|  | 5 | 10 | 0 | −25 | +2 | 0 | −7 | +5 | 120 | 100 | −2 | 0 | −9 |
| according to Example 67 | 30 | 10 | −100 | −82 | −25 | −38 | −48 | +3 | 1,130 | 180 | 0 | −12 | −56 |
| clofibrate | 100 | 10 | +12 | −16 | −36 | +8 | −3 | +8 | 130 | 130 | +28 |  |  |
| bezafibrate | 50 | 10 | 0 | −31 | −21 | +23 | −23 | +29 | 110 | 150 | +39 |  |  |

Influence on the serum lipoproteins, the relative liver weight, the trend in body weight and the feed consumption of ♂ rats after oral treatment for 7 days.

TABLE IV

| Compound | Dose mg/kg/ day | Number of animals | CHOLESTEROL in VLDL | CHOLESTEROL in LDL | CHOLESTEROL in HDL | PROTEIN in VLDL | PROTEIN in LDL | PROTEIN in HDL | GLYCEROL in VLDL | GLYCEROL in HDL | GLYCEROL in LDL | Relative liver weight | HDL VLDL + LDL Cholesterol | HDL VLDL + LDL Protein |
|---|---|---|---|---|---|---|---|---|---|---|---|---|---|---|
| according to Example 1 | 30 | 10 | −100 | −36 | −3 | −38 | −17 | −5 | −60 | −2 | +9 | +9 | 180 | 130 |
|  | 3 | 10 | −58 | −2 | −1 | −19 | −4 | −3 | −33 | −8 | −7 | 0 | 130 | 110 |

Influence on the serum lipoproteins and the relative liver weight after oral treatment of ♂ Wistar rats for 4 weeks.

and its analogs greatly increase the relative liver weight, while the new compounds are neutral in this respect.

The tests were carried out as described below: male rates of the HOE: WISFf (SPF 71) strain with an initial weight of more than 220 g, in groups of 10 animals in each case, were given the indicated dose of the compound to be tested, in PEG 400 by probang once per day (in the morning); the control group was given only PEG 400. A total of 7 or 28 administrations were made, the final administration (7th or 28th administration) being made 24 hours before taking blood samples and killing. The animals had free access to feed and water during the test. The feed was withdrawn 24 hours before taking the blood samples; the samples were taken retroorbitally under slight ether narcosis. Immediately after taking the blood samples, the animals were killed by distortion of the spinal column. The livers were removed and the relative liver weight was determined. In addition, the trend in body weight and the feed consumption were examined.

For analysis of the serum lipoproteins, the serum from all the rats in one group was pooled. The serum lipoproteins were separated into VLDL, LDL and The compounds can therefore be used as appetite depressants for the treatment of adiposity, on its own or in combination with other disturbances of the lipometabolism. The dose to be administered per day is 2 to 2,000 mg and preferably 2 to 200 mg, and this amount is appropriately administered in relative small doses of 0.2 to 50 mg twice to four times per day or in a form having a delayed action.

On the basis of their pharmacological properties, the new compounds of the general formula I can be used in the form of the free bases and/or in the form of their pharmaceutically acceptable acid addition salts as medicaments and they are administered either on their own or as a mixture with suitable excipients and/or acceptable diluents and optionally also with other additives.

The invention thus also relates to medicaments, especially for the treatment of adiposity, which consist of at least one compound of the formula I, optionally in the form of its physiologically acceptable salts, or which contain this active ingredient. The compounds are usually present together with the conventional pharmaceutically acceptable excipients and/or diluents. The preparations can be administered orally, rectally or parenterally. Suitable solid or liquid galenical formulations are, for example, tablets, dragees, powders, capsules, suppositories, syrups, emulsions, suspensions, drops or injectable solutions and also preparations with a delayed release of the active ingredient. Examples which may be mentioned of excipients and diluents frequently used are diverse sugars or types of starch, cellulose derivatives, magnesium carbonate, gelatin, animal and vegetable oils, polyethylene glycols, water or other suitable solvents.

Preferably, the preparations can be prepared in dosage units. In particular, tablets, capsules, suppositories and ampoules are examples of suitable dosage units. Each dosage unit can contain up to 1,000 mg, but preferably 1 to 200 mg of the active ingredient.

The uncorrected melting points (m.p.) given in the examples which follow are in most cases decomposition temperatures. The IR spectra were recorded in KBr using a model 157 Perkin Elmer spectrophotometer (NaCl prism) and the IR spectroscopic data given are in each case based on a polystyrene calibration band at $6.24\mu$.

EXAMPLE 1

A mixture of 14.2 g (50 mmoles) of ethoxymethylene-cyanoacetic acid 3-trifluoromethyl-anilide, 50 ml of 1,2-dimethoxyethane, 8.6 g (55 mmoles) of 1-amidino-4,4-dimethyl-imidazolidin-2-one and 50 ml of isopropanol was stirred for 30 minutes at room temperature and for 1.5 hours while boiling under reflux. After cooling, the solid was filtered off and washed thoroughly with acetone. The crystalline substance was then recrystallized from 800 ml of ethanol, the hot solution being filtered. 10.5 g (53.3%) of pure 4-amino-2-(4,4-dimethyl-imidazolidin-2-on-1-yl)-pyrimidine-5-carboxylic acid 3-trifluoromethyl-anilide of m.p. 293°–4° C. were obtained; IR: (ureido+C=O $5.82\mu$. A further 7.3 g (37%) of pure product of m.p. 293°–4° C. were obtained from the combined mother liquors by crystallization from ethanol.

Analysis: $C_{17}H_{17}F_3N_6O_2$: calculated (%): C 51.8; H 4.3; F 14.4; N 21.3, molecular weight 394.4. found (%): C 51.7; H 4.3; N 21.0.

EXAMPLE 2

A mixture of 14.2 g (50 mmoles) of ethoxymethylene-cyanoacetic acid 3-trifluoromethyl-anilide, 8.6 g (55 mmoles) of 1-amidino-4,4-dimethyl-imidazolidin-2-one and 80 ml of acetonitrile was stirred for 20 minutes at 40° C. and for 2 hours while boiling under reflux, cooled to 15° C. and filtered. According to thin layer chromatography, the crystalline substance isolated (10.8 g) was virtually pure 4-amino-2-(4,4-dimethylimidazolidin-2-on-1-yl)-pyrimidine-5-carboxylic acid 3-trifluoromethyl-anilide (melting point 292°–93° C.). After concentrating the filtrate and recrystallizing the resulting solid from acetonitrile, a further 7.2 g of the above-mentioned pyrimidine derivative (m.p. 293°–4° C.) were obtained and the yield was thus 91.5%.

A batch which was carried out analogously but in which absolute ethanol was used in place of acetonitrile as the solvent gave, after isolation of the solid first obtained and working up of the ethanolic mother liquors by concentrating and recrystallizing the further crystalline substances obtained, a total of 88.5% of theory of 4-amino-2-(4,4-dimethyl-imidazolidin-2-on-1-yl)-pyrimidine-5-carboxylic acid 3-trifluoromethylanilide of m.p. 293°–4° C.

EXAMPLE 3

A mixture of 13.25 g (50 mmoles) of ethoxymethylene-cyanoacetic acid 3-chloro-2-methyl-anilide, 8.7 g (56 mmoles) of 1-amidino-4,4-dimethyl-imidazolidin-2-one, 100 ml of 1,2-dimethoxyethane and 50 ml of isopropanol was stirred for 30 minutes at room temperature, for 30 minutes at 60° C. and for 1.5 hours while boiling under reflux, then cooled to 15° C. and filtered. The filter residue was washed with acetone and dried at 90° C. in vacuo. 18.25 g (97.3%) of 4-amino-2-(4,4-dimethylimidazolidin-2-on-1-yl)-pyrimidine-5-carboxylic acid 3-chloro-2-methyl-anilide of m.p. 287°–8° C. were obtained;

IR: (ureido+C=O: $5.80\mu$.

Analysis: $C_{17}H_{19}ClN_6O_2$: calculated (%): C 54.5; H 5.1; Cl 9.5; N 22.4, molecular weight 374.9. found (%): C 54.2; H 5.1; Cl 9.8; N 22.2.

A batch which was carried out analogously but in which only 100 ml of isopropanol were used in place of dimethoxyethane and isopropanol as the solvent and diluent gave, after working up the mother liquors, a total of 17.8 g (94.5%) of pure 4-amino-2-(4,4-dimethylimidazolidin-2-on-1-yl)-pyrimidine-5-carboxylic acid 3-chloro-2-methyl-anilide of m.p. 286°–8° C.

EXAMPLE 4

A mixture of 13,25 g (50 mmoles) of ethoxymethylene-cyanoacetic acid 3-chloro-4-methyl-anilide, 8.6 g (55 mmoles) of 1-amidino-4,4-dimethyl-imidazolidin-2-one, 100 ml of 1,2-dimethoxyethane and 50 ml of isopropanol was stirred for 30 minutes at room temperature and for 2 hours while boiling under reflux, then cooled to 15° C. and filtered. The filter residue was washed with acetone and dried at 90° C. in vacuo. 17.4 g (93%) of 4-amino-2-(4,4-dimethyl-imidazolidin-2-on-1-yl)pyrimidine-5-carboxylic acid 3-chloro-4-methyl-anilide of m.p. 290°–2° C. were obtained. After concentrating the filtrate, a further 1.27 g (6.8%) of this product with a m.p. of 292°–3° C. (decomposition) were obtained;

IR: (ureido+C=O $5.76\mu$.

Analysis: $C_{17}H_{19}ClN_6O_2$: calculated (%): C 54.5; H 5.1; Cl 9.5; N 22.4, molecular weight 374.9. found (%): C 54.0; H 5.1; Cl 9.4; N 22.2.

The 4-amino-2-(imidazolidin-2-on-1-yl)-pyrimidine-5-carbanilides listed in Table 2 below (Examples 5–24a and b) were prepared by an analogous procedure.

TABLE 2(++)

[Structure: imidazolidinone-pyrimidine-carboxanilide with substituents R$^{11}$, R$^{12}$, R$^{13}$ on imidazolidine ring, R$^7$ and (R$^8$)$_n$ on anilide phenyl ring; NH$_2$ on pyrimidine]

| Ex. No. | R$^{11}$ | R$^{12}$ | R$^{13}$ | R$^7$ | R$^8$ | n | m.p. °C.(xx) | Yield in % |
|---|---|---|---|---|---|---|---|---|
| 5 | H | H | H | 4-Cl | — | 0 | 236–7 | 83 |
| 6 | CH$_3$ | H | H | 3-CF$_3$ | — | 0 | 299–300 | 83 |
| 7 | CH$_3$ | H | H | 3-Cl | 2-CH$_3$ | 1 | 252–3 | 68(+) |
| 8 | CH$_3$ | H | H | 3-Cl | 4-OC$_2$H$_5$ | 1 | 231–2 | 87 |
| 9 | CH=CH$_2$ | H | H | 3-CF$_3$ | — | 0 | 271–3 | 80 |
| 10 | CH$_3$ | H | CH$_3$ | 3-CF$_3$ | — | 0 | 272–4 | 42 |
| 11 | CH$_3$ | CH$_3$ | H | 4-Cl | — | 0 | 291–2 | 85 |
| 12 | CH$_3$ | CH$_3$ | H | 3-Cl | 4-OC$_2$H$_5$ | 1 | 266–8 | 86 |
| 13 | CH$_3$ | CH$_3$ | H | 4—O—(phenyl-CH$_3$,CH$_3$) | 3-Cl | 1 | 260–1 | 95 |
| 14 | CH$_3$ | CH$_3$ | H | 4-CH(CH$_3$)$_2$ | 3-Cl | 1 | 303–5 | 94 |
| 15 | CH$_3$ | CH$_3$ | H | 4-Cl | 2-CH$_3$ | 1 | 277–8 | 84 |
| 16 | CH$_3$ | CH$_3$ | H | 4-Cl | 3-CH$_3$ | 1 | 282–4 | 95 |
| 17 | CH$_3$ | CH$_3$ | H | 2-Cl | 6-CH$_3$ | 1 | 165–73 | 80 |
| 18 | CH$_3$ | CH$_3$ | H | 5-Cl | 2-CH$_3$ | 1 | 242–4 | 84 |
| 19 | CH$_3$ | CH$_3$ | H | 2-Cl | 4-NO$_2$ | 1 | 286–8 | 72 |
| 20 | CH$_3$ | CH$_3$ | H | 4-CH(CH$_3$)$_2$ | H | 0 | 299–300 | 97 |
| 21 | CH$_3$ | CH$_3$ | H | 2-CH$_3$ | 4-CH$_3$, 6-CH$_3$ | 2 | 218–20 | 58 |
| 22 | CH$_3$ | CH$_3$ | H | 2-OCH$_3$ | 4-OCH$_3$, 5-OCH$_3$ | 2 | 240–1 | 80 |
| 23 | CH$_3$ | CH$_3$ | H | 4-OC$_6$H$_5$ | 3-Cl, 6-CH$_3$ | 2 | 262–3 | 89 |
| 24 a | CH$_3$ | CH$_3$ | H | 3,4-O-CH$_2$—O— | | 1 | 310–11 | 70 |
| 24 b | CH$_3$ | CH$_3$ | H | 4-COOC$_2$H$_5$ | — | 0 | 294–5 | 69 |

+(4-R)-configuration in the imidazolidine ring;
xxIn the majority of cases, the melting points are decomposition temperatures
++The compounds obtained according to Examples 5–24b gave the correct analytical values corresponding to the empirical formulae. In the IR spectrum, these compounds have a characteristic, intense band of the imidazolidinone carbonyl at 5.76–5.82 μ.

EXAMPLE 25

0.65 g (22 mmoles) of an 80% strength suspension of sodium hydride in paraffin oil was added in portions, at room temperature, in the course of 15 minutes to a mixture of 4.74 g (20 mmoles) of 1-amidino-4,5-dimethylimidazolidin-2-one hydrobromide (threo/erythro mixture), 5.30 g (20 mmoles) of ethoxymethylenecyanoacetic acid 3-chloro-4-methyl-anilide and 80 ml of absolute 1,2-dimethoxyethane, whilst stirring. The mixture was stirred for a further 20 minutes at room temperature and for 2 hours while boiling under reflux. The solid was then filtered off and washed with water. The filtrate was evaporated in vacuo, the residue was mixed with acetone and the solid was filtered off. The two portions of solid (6.60 g) were combined and boiled thoroughly with 300 ml of methanol and the mixture was filtered. The methanol extract was evaporated in vacuo and the residue which remained was crystallized from acetone. A solution of 2.6 g of NaHCO$_3$ in 90 ml of water was added to the crystalline product (4.0 g) and the mixture was shaken for 24 hours. It was then filtered and the solid was washed thoroughly with water and dried. This gave 3.30 g (44%) of pure 4-amino-2-(4,5-dimethyl-imidazolidin-2-on-1-yl)-pyrimidine-5-carboxylic acid 3-chloro-4-methylanilide of m.p. 252°–3° C.;

IR: (ureido+-CO: 5.80μ.

Analysis: C$_{17}$H$_{19}$ClN$_6$O$_2$: calculated (%): C 54.5; H 5.1; Cl 9.5; N 22.4 molecular weight 374.9. found (%): C 54.2; H 5.1; Cl 9.8; N 22.7, molecular weight 374;376 (by mass spectroscopy).

EXAMPLE 26

7.1 g (30 mmoles) of 1-amidino-4,5-dimethylimidazolidin-2-one hydrobromide (threo/erythro mixture) were added in portions, at −2° C. to 0° C., to a solution of 0.69 g of sodium in 50 ml of absolute ethanol. The mixture was stirred for a further 15 minutes at 20°–23° C. and a suspension of 8.0 g (30 mmoles) of ethoxymethylenecyanoacetic acid 3-chloro-2-methyl-anilide in 50 ml of 1,2-dimethoxyethane was then added. After stirring for 15 minutes at room temperature and for 2 hours while boiling under reflux, the reaction solution was evaporated in vacuo. A solution of 6 g of NaHCO$_3$ in 200 ml of water was added to the residue. The mixture was shaken for 8 hours at room temperature and the solid was then filtered off and washed with water and the product was dried. 8.2 g (73%) of 4-amino-2-(4,5-dimethylimidazolidin-2-on-1-yl)-pyrimidine-5-carboxylic acid 3-chloro-2-methyl-anilide of m.p. 226°–7° C. (IR: (ureido+-CO: 5.85μ) were thus obtained.

Analysis: C$_{17}$H$_{19}$ClN$_6$O$_2$: found (%): C 54.2; H 5.1; Cl 9.8; N 22.0, molecular weight 374;376 (by mass spectroscopy).

EXAMPLE 27

A solution of 0.28 g (12 mg atom) of sodium in 18 ml of absolute ethanol was added dropwise at −3° C. to 0° C. to a solution of 4.0 g (about 15 mmoles) of crude, oily 1-amidino-4-methyl-4-propyl-imidazolidin-2-one hydrobromide in 10 ml of absolute ethanol. The mixture was stirred for 15 minutes at room temperature. A suspension of 3.52 g (12 mmoles) of ethoxymethylene-cyanoacetic acid 3-chloro-4-isopropyl-anilide in 17 ml of 1,2-dimethoxyethane was then added and the resulting mixture was stirred for 20 minutes at room temperature and for 3 hours while boiling under reflux. After cooling, the mixture was filtered and the filter residue was washed with acetone. The filtrate was evaporated in vacuo and the residue which remained was suspended in water. The suspension was filtered and the solid was washed with water. The two portions of solid were combined and shaken for 3 hours with a solution of 2.5 g of NaHCO$_3$ in 100 ml of water. The mixture was then filtered and the solid was washed with water and, after drying, recrystallized from methanol. Together with a second crystalline product obtained after concentrating the mother liquor, 4.80 g (93% based on 12 mmoles) of pure 4-amino-2-(4-methyl-4-propyl-imidazolidin-2-on-1-yl)-pyrimidine-5-carboxylic acid 3-chloro-4-isopropylanilide of m.p. 252°–4° C. were obtained in this way.

Analysis: $C_{21}H_{27}ClN_6O_2$: calculated (%): C 58.5; H 6.3; Cl 8.2; N 19.5, molecular weight 430.9. found (%): C 58.4; H 6.3; Cl 8.4; N 19.6.

EXAMPLE 28

Using 10.9 g (41 mmoles) of crude, oily 1-amidino-4-methyl-4-propyl-imidazolidin-2-one hydrobromide and 8.75 g (33 mmoles) of ethoxymethylene-cyanoacetic acid 3-chloro-2-methyl-anilide as the starting materials, 10.4 g (78% based on 33 mmoles) of pure 4-amino-2-(4-methyl-4-propyl-imidazolidin-2-on-1-yl)-pyrimidine-5-carboxylic acid 3-chloro-2-methyl-anilide of m.p. 252°–3° C. were obtained by a procedure the same as that described in Example 27.

Analysis: $C_{19}H_{23}ClN_6O_2$: calculated (%): C 56.6; H 5.8; Cl 8.8; N 20.9, molecular weight 402.9. found (%): C 56.3; H 5.8; Cl 8.6; N 20.4, molecular weight 402; 404 (mass spectroscopy).

EXAMPLE 29

A mixture (solution) of 9.6 g (62 mmoles) of 1-amidino-4,4-dimethyl-imidazolidin-2-one, 18.4 g (60 mmoles) of crude, oily ethoxymethylene-cyanoacetic acid N-benzylanilide, 180 ml of dimethoxyethane and 120 ml of isopropanol was stirred for 20 minutes at room temperature and for 3 hours while boiling under reflux and then evaporated in vacuo. The oily residue (27 g) was absorbed from 80 ml of CH$_2$Cl$_2$ on a 43 cm high ($\phi$=5.0 cm) silica gel S (0.063–0.2 mm, Riedel-DeHäen AG)/CH$_2$Cl$_2$ column and chromatographed. After elution with 1,200 ml of CH$_2$Cl$_2$, 600 ml of 100:1 CH$_2$Cl$_2$/C$_2$H$_5$OH, 600 ml of 100:2 CH$_2$Cl$_2$/C$_2$H$_5$OH, 600 ml of 100:3 CH$_2$Cl$_2$/C$_2$H$_5$OH and 600 ml of 100:4 CH$_2$Cl$_2$/C$_2$H$_5$OH, 4.40 g of 5-cyano-2-(4,4-dimethyl-imidazolidin-2-on-1-yl)-3,4-dihydro-4-oxo-pyrimidine (m.p. 273°–4° C.) were eluted with 600 ml of 100:5 CH$_2$Cl$_2$/C$_2$H$_5$OH and 600 ml of 100:6 CH$_2$Cl$_2$/C$_2$H$_5$OH, and on further elution with 200 ml of 100:7 CH$_2$Cl$_2$/C$_2$H$_5$OH, 600 ml of 100:8 CH$_2$Cl$_2$/C$_2$H$_5$OH and 600 ml of 100:9 CH$_2$Cl$_2$/C$_2$H$_5$OH, 3.50 g of product were eluted in which the desired compound was greatly enriched. These 3.5 g were recrystallized from methanol and 2.60 g (10.5%) of pure 4-amino-2-(4,4-dimethyl-imidazolidin-2-on-1-yl)-pyrimidine-5-carboxylic acid N-benzyl-anilide of m.p. 276°–7° C. (IR: (ureido+CO 5.79μ) were obtained.

Analysis: $C_{23}H_{24}N_6O_2$: calculated (%): C 66.3; H 5.8; N 20.2, molecular weight 416.5. found (%): C 65.9; H 5.7; N 19.8, molecular weight 416.0 (by mass spectroscopy).

EXAMPLE 30

A mixture of 5.78 g (30 mmoles) of 1-amidino-4,4-dimethyl-imidazolidin-2-one hydrochloride, 2.30 g (16.5 mmoles) of K$_2$CO$_3$, 70 ml of acetonitrile and 7.5 g (30 mmoles) of ethoxymethylene-cyanoacetic acid 4-chloroanilide was stirred for 1 hour at 60° C. and for 5 hours while stirring under reflux and then evaporated in vacuo. 70 ml of water were added to the residue, the mixture was shaken thoroughly and the solid was filtered off and washed thoroughly with water and acetone. After drying, 8.33 g (77%) of 4-amino-2-(4,4-dimethyl-imidazolidin-2-on-1-yl)-pyrimidine-5-carboxylic acid 4-chloroanilide of m.p. 290°–1° C. were obtained.

EXAMPLE 31

A mixture of 2.37 g (10 mmoles) of 1-amidino-4,4-dimethyl-imidazolidin-2-one hydrobromide, 1.10 g of triethylamine, 60 ml of methylene chloride and 2.60 g (10 mmoles) of ethoxymethylene-cyanoacetic acid 4-isopropyl-anilide was boiled under reflux for 4 hours. The solvent was then evaporated. 50 ml of water were added to the residue, the mixture was shaken for 10 minutes, the solid was filtered off and washed with water, and a solution of 1.7 g of NaHCO$_3$ in 50 ml of water was then added and the mixture was shaken for 3 hours at room temperature. The mixture was then filtered and the filter residue was washed successively with water and acetone and dried. 2.91 g (79%) of pure 4-amino-2-(4,4-dimethyl-imidazolidin-2-on-1-yl)-pyrimidine-5-carboxylic acid 4-isopropyl-anilide of m.p. 299°–300° C. were obtained.

EXAMPLE 32

A solution of 0.28 g (12 mg atom) of sodium in 18 ml of absolute ethanol was added dropwise at −5° to 0° C. to a solution of 4.0 g (about 15 mmoles) of crude, oily 1-amidino-4,4-diethyl-imidazolidin-2-one hydrobromide in 10 ml of absolute ethanol and the mixture was stirred for 15 minutes at 23° C. A suspension of 3.24 g (10 mmoles) of ethoxymethylene-cyanoacetic acid 4-phenylthio-anilide in 15 ml of 1,2-dimethoxyethane was then added and the resulting mixture was stirred for 30 minutes at 24° and for 3 hours while boiling under reflux. After cooling, the mixture was filtered and the filter residue was washed with water and acetone. The residue which remained after evaporating the filtrate was suspended in water. The suspension was filtered and the solid was washed with water. A solution of 2.5 g of NaHCO$_3$ in 100 ml of water was added to the two portions of solid and the mixture was shaken for 4 hours. After filtering off, the solid was washed with water and recrystallized from 10:1 methanol/dimethylformamide. Together with a second crystalline product obtained after evaporating the mother liquor and again recrystallizing the residue from methanol, 3.65 g (79%, based on 10 mmoles) of pure 4-amino-2-(4,4-diethyl-imidazolidin-2-on-1-yl)-pyrimidine-5-carboxylic acid 4-phenylthio-anilide of m.p. 265°-6° C. (IR: (ureido+CO: 5.81μ) were obtained in this way.

Analysis: $C_{24}H_{26}N_6O_2S$: calculated (%): C 62.3; H 5.7; N 18.2; S 6.9, molecular weight 462.6. found (%): C 62.1; H 5.8; N 17.8; S 6.7.

EXAMPLE 33

Using 6.9 g (26 mmoles) of crude, oily 1-amidino-4-methyl-4-propyl-imidazolidin-2-one hydrobromide and 6.0 g (21 mmoles) of ethoxymethylenecyanoacetic acid 3-trifluoromethyl-anilide as the starting materials, 6.6 g (79% based on 21 mmoles) of pure 4-amino-2-(4-methyl-4-propyl-imidazolidin-2-on-1-yl)-pyrimidine-5-carboxylic acid 3-trifluoromethyl-anilide of m.p. 248°-9° C. were obtained by a procedure the same as that described in Example 27 (the crude product had been recrystallized from acetone).

Analysis: $C_{19}H_{21}F_3N_6O_2$: calculated (%): C 54.0; H 5.0; F 13.5; N 19.9, molecular weight 422.4. found (%): C 53.8; H 5.3; F 13.5; N 19.6, molecular weight 422.0 (by mass spectroscopy).

EXAMPLE 34

(a) 4-Amino-2-(4,4-dimethyl-imidazolidin-2-on-1-yl)-pyrimidine-5-carboxylic acid 3-chloro-2-methyl-anilide hydrochloride:

3.24 ml of a 6.3 molar solution of HCl in ether were added dropwise, with cooling, to a suspension of 7.50 g (20 mmoles) of 4-amino-2-(4,4-dimethyl-imidazolidin-2-on-1-yl)-pyrimidine-5-carboxylic acid 3-chloro-2-methyl-anilide in 120 ml of absolute ethanol and the resulting slurry was then shaken for 1 hour at room temperature. It was then filtered and the hydrochloride was washed with ethanol and ether and dried. 8.15 g of the abovementioned hydrochloride of m.p. 300°-302° C. were obtained.

Analysis: $C_{17}H_{20}Cl_2N_6O_2$: calculated (%): C 49.6; H 4.9; Cl 17.2; N 20.4. found (%): C 49.3; H 5.1; Cl 17.1; N 20.0 Cl$^\theta$8.6.

(b) 4-Amino-2-(4,4-dimethyl-imidazolidin-2-on-1-yl)-pyrimidine-5-carboxylic acid 5-chloro-2-methyl-anilide hydrochloride was prepared analogously to this procedure; m.p. 293°-5° C.

Analysis: $C_{17}H_{20}Cl_2N_6O_2$: found (%): C 49.3; H 5.1; Cl 17.2; N 20.0 Cl−8.8.

(c) 4-Amino-2-(4,4-dimethyl-imidazolidin-2-on-1-yl)-pyrimidine-5-carboxylic acid 3-trifluoromethyl-anilide hydrochloride was prepared analogously to the procedure described under a); m.p. 318°-9° C.

Analysis: $C_{17}H_{18}ClF_3N_6O_2$: calculated (%): C 47.4; H 4.2; N 19.5 Cl$^\theta$8.2. found (%): C 47.2; H 4.2; N 19.2 Cl$^\theta$8.0.

EXAMPLE 35

4-Amino-2-(4,4-dimethyl-imidazolidin-2-on-1-yl)-pyrimidine-5-carboxylic acid 3-trifluoromethyl-anilide p-toluenesulfonate.

A hot solution of 0.95 g (5 mmoles) of p-toluenesulfonic acid hydrate in 5 ml of absolute ethanol was added to a hot suspension of 1.97 g (5 mmoles) of 4-amino-2-(4,4-dimethylimidazolidin-2-on-1-yl)-pyrimidine-5-carboxylic acid 3-trifluoromethyl-anilide in 40 ml of absolute ethanol; after this, a solution formed for a short time and this was boiled under reflux for 5 minutes. After cooling, the crystalline product which had precipitated was filtered off and washed with ethanol and ether. After drying, 2.52 g ($\triangleq$ 86.3% yield) of the above-mentioned p-toluenesulfonate of m.p. 223°-4° C. were obtained.

Analysis: $C_{24}H_{25}F_3N_6O_5S$: calculated (%): C 50.9; H 4.4; F 10.1; N 14.8; S 5.7. found (%): C 50.5; H 4.5; F 9.8; N 14.5; S 5.9.

EXAMPLE 36

5.0 g (52 mmoles) of guanidinium chloride were added to a solution of 1.15 g of sodium in 60 ml of isopropanol. The mixture was boiled under reflux for 20 minutes and, after cooling, the NaCl which had precipitated was filtered off. A solution of 5.0 g (50 mmoles) of butyl isocyanate in 20 ml of 1,2-dimethoxyethane was added dropwise to the filtrate at −10° C. in the course of 15 minutes, the resulting mixture was stirred for a further 30 minutes at 0°, 30 minutes at 25° C. and 1 hour at 40° C. and cooled to room temperature. 13.2 g (50 mmoles) of ethoxymethylene-cyanoacetic acid 4-chloro-2-methyl-anilide were added and the suspension was stirred for 20 minutes at room temperature and for 2 hours while boiling under reflux. After cooling, the solid was filtered off and washed with acetone. 8.2 g of a crystalline crude product were thus obtained. A further 3.6 g of this substance were obtained by concentrating the filtrate. The solid was recrystallized from 4:1 acetonitrile/dimethylformamide and 10.84 g (58%) of pure 4-amino-2-(3-butyl-1-ureido)-pyrimidine-5-carboxylic acid 4-chloro-2-methyl-anilide of m.p. 263°-4° C. were obtained.

Analysis: $C_{17}H_{21}ClN_6O_2$: calculated (%): C 54.2; H 5.6; Cl 9.4; N 22.3, molecular weight 376.9. found (%): C 53.8; H 5.5; Cl 9.4; N 22.4, molecular weight 376; 378 (by mass spectroscopy).

EXAMPLE 37

3.0 g (31 mmoles) of guanidinium chloride were added to a solution of 0.69 g of sodium in 40 ml of isopropanol. The mixture was boiled under reflux for 20 minutes and, after cooling, the NaCl which had precipitated was filtered off at about 10° C. A solution of 4.2 g (33.5 mmoles) of cyclohexyl isocyanate in 20 ml of absolute dimethoxyethane was added dropwise to the filtrate at −10° C. in the course of 25 minutes. The mixture was stirred for a further 30 minutes at from −10° C. to room temperature, 30 minutes at room temperature and 1 hour at 40° C. and cooled to room temperature. 8.55 g (30 mmoles) of ethoxymethylene-cyanoacetic acid 3-trifluoromethylanilide were added and the mixture was stirred for 20 minutes at room temperature and for 2.5 hours whilst boiling under reflux. Crystalline product precipitated on cooling and this was filtered off and washed with acetone. 5.2 g (41%) of pure 4-amino-2-(3-cyclohexyl-1-ureido)-pyrimidine-5-carboxylic acid 3-trifluoromethylanilide of m.p. 268°-9° C. were obtained in this way.

Analysis: $C_{19}H_{21}F_3N_6O_2$: calculated (%): C 54.0; H 5.0; F 13.5; N 19.9, molecular weight 422.4. found (%): C 53.8; H 5.1; F 13.2; N 19.8, molecular weight 422.0 (by mass spectroscopy).

The 4-amino-2-ureido-pyrimidine-5-carbanilides listed in Table 3 (Examples 38–54) were prepared by a procedure analogous to that described in Examples 36 and 37. The isolation of the particular end product was in some cases effected by the procedure described in Example 36, that is to say further amounts of crude product were obtained by concentrating or evaporating the filtrate and the total crude product was recrystallized from dimethylformamide/acetonitrile; in the case of some of the examples, the end product was obtained directly in a pure form, as in Example 37, and no further amount of this product was obtained from the concentrated filtrate. The yields of the compounds obtained in Examples 38–54 (Table 3) were between 39 and 63%.

TABLE 3++

Example 38-54

[Structure: pyrimidine with NH2, N-C(=O)-NH-R2 ureido group, and carboxamide C(=O)-NH-phenyl with R7 and (R8)n substituents]

| Example No. | R² | R⁷ | R⁸ | n | m.p. °C.* |
|---|---|---|---|---|---|
| 38 | CH₃ | H | — | 0 | 252–4 |
| 39 | C₄H₉ | 4-CH(CH₃)₂ | 3-Cl | 1 | 252–3 |
| 40 | C₄H₉ | 4-OC₂H₅ | 3-Cl | 1 | 259–60 |
| 41 | C₄H₉ | 4-OC₆H₅ | 3-Cl 6-CH₃ | 2 | 255–6 |
| 42 | tert.-C₄H₉ | 3-Cl | 2-CH₃ | 1 | 247–8 |
| 43 | tert.-C₄H₉ | 4-OC₂H₅ | 3-Cl | 1 | 246–8 |
| 44 | tert.-C₄H₉ | 3-CF₃ | — | 0 | 261–2 |
| 45 | C₆H₁₁ (cyclohexyl) | 3-Cl | 2-CH₃ | 1 | 252–3 |
| 46 | C₈H₁₇ | 3-Cl | 2-CH₃ | 1 | 263–4 |
| 47 | C₈H₁₇ | 4-OC₂H₅ | 3-Cl | 1 | 264–5 |
| 48 | H₃C(CH₂)₄—CH(CH₃)— | 3-CF₃ | — | 0 | 259–60 |
| 49 | C₆H₅ | 4-OCH₃ | — | 0 | 277–9 |
| 50 | 4-CF₃-C₆H₄ | 4-Cl | 3-CH₃ | 1 | 281–3 |
| 51 | 4-CH₃-C₆H₄ | 4-OC₂H₅ | 3-Cl | 1 | 279–81 |
| 52 | 4-Cl-C₆H₄ | 4-OC₆H₅ | H | 0 | 282–3 |
| 53 | C₆H₅ | 3-Cl | 2-CH₃ | 1 | 298–300 |
| 54 | C₄H₉ | 3-Cl | 2-CH₃ | 1 | 250–1 |

++The compounds obtained according to Examples 38–54 gave the correct analytical values and molecular weights (determined by mass spectroscopy) corresponding to the empirical formulae.
*The melting points are decomposition temperatures.

EXAMPLE 55

(a) 2,4-Diamino-pyrimidine-5-carboxylic acid 3-chloro-2-methyl-anilide:

10 g (105 mmoles) of guanidinium chloride were added to a solution of 2.3 g of sodium in 160 ml of isopropanol. The mixture was boiled under reflux for 20 minutes and, after cooling, the NaCl which had precipitated was filtered off. A suspension of 26.5 g (0.1 mole) of ethoxymethylene-cyanoacetic acid 3-chloro-2-methyl-anilide in 100 ml of dioxan was added to the filtrate and the mixture was stirred for 20 minutes at room temperature, for 20 minutes at 60° C. and for 1.5 hours while boiling under reflux.

The mixture was cooled and the solid was filtered off and washed with methanol. After concentrating the filtrate, further solid precipitated and this was isolated in the same way. A total of 23.6 g of crude product was obtained and this, when recrystallized from 3:1 acetonitrile/dimethylformamide, gave, including the product obtained from working up the concentrated mother liquor, 20.3 g (73%) of pure 2,4-diamino-pyrimidine-5-carboxylic acid 3-chloro-2-methyl-anilide of m.p. 291°–2° C.

Analysis: $C_{12}H_{12}ClN_5O$: calculated (%): C 51.9; H 4.4; Cl 12.8; N 25.2, molecular weight 277.7. found (%): C 51.8; H 4.4; Cl 13.1; N 25.1, molecular weight 277; 279 (by mass spectroscopy).

(b) 4-Amino-2-(3-butyl-1-ureido)-pyrimidine-5-carboxylic acid 3-chloro-2-methyl-anilide:

A mixture of 2.78 g (10 mmoles) of 2,4-diamino-pyrimidine-5-carboxylic acid 3-chloro-2-methyl-anilide, 35 ml of dry dimethylformamide, 1.40 g (14 mmoles) of butyl isocyanate and 0.40 g (4 mmoles) of triethylamine was warmed at 85° C. for 16 hours, whilst stirring, and then evaporated in vacuo. The residue was twice boiled for 1 hour with 50 ml of methanol in each case and after each operation the solid which had not dissolved was filtered off in the cold state. This solid was recrystallized from 5:1 acetonitrile/dimethylformamide, and 1.38 g (37%) of pure 4-amino-2-(3-butyl-1-ureido)-pyrimidine-5-carboxylic acid 3-chloro-2-methyl-anilide of m.p. 249°–51° C. were obtained. According to the IR spectrum, the melting point and the mixed melting point, this compound proved to be identical to that obtained according to Example 54 (Table 2) by another route.

The following 2,4-diamino-pyrimidine-5-carbanilides were prepared by the procedure described under (a):

2,4-diamino-pyrimidine-5-carboxylic acid 4-chloro-3-methyl-anilide; m.p. 246°–47° C.; analysis: found (%): C 51.6 H 4.3 Cl 12.7 N 24.8 molecular weight 277; 279 (by mass spectroscopy)

2,4-diamino-pyrimidine-5-carboxylic acid 3-chloro-4-ethoxy-anilide, m.p. 245°–6° C.;

Analysis: $C_{13}H_{14}ClN_5O_2$: found (%): C 50.8; H 4.5; Cl 12.1; N 22.8, molecular weight 307;309 (by mass spectroscopy). calculated (%): C 50.7; H 4.6; Cl 11.5; N 22.8, molecular weight 307.7.

2,4-diamino-pyrimidine-5-carboxylic acid 3-trifluoromethyl-anilide, m.p. 223°–4° C.;

Analysis: $C_{12}H_{10}F_3N_5O$: calculated (%): C 48.5; H 3.4; F 19.2; N 23.6, molecular weight 297.3. found (%): C 48.6; H 3.4; F 19.3; N 23.4, molecular weight 297 (by mass spectroscopy).

The following 4-amino-2-ureido-pyrimidine-5-carbanilides were prepared by the procedure described under (b):

4-amino-2-(3-phenyl-1-ureido)-pyrimidine-5-carboxylic acid 3-chloro-2-methyl-anilide; m.p. 298°–300° C. (decomposition); yield 16%.

Analysis: $C_{19}H_{17}ClN_6O_2$: calculated (%): C 57.5; H 4.3; Cl 8.9; N 21.2, found (%): C 57.0; H 4.1; Cl 8.5; N 21.5.

4-amino-2-(3-(3,4-methylenedioxy-phenyl)-1-ureido)-pyrimidine-5-carboxylic acid 4-chloro-3-methyl-anilide; m.p. 276°–7° C. (from DMF/acetonitrile) (yield 18%).

Analysis: $C_{20}H_{17}ClN_6O_4$: calculated (%): C 54.5; H 3.9; Cl 8.0; N 19.1, molecular weight 440.9. found (%): C 53.9; H 3.9; Cl 7.9; N 18.8, molecular weight 440; 442 (by mass spectroscopy).

EXAMPLE 56

3.0 g (31 mmoles) of guanidinium chloride were added to a solution of 0.69 g of sodium in 40 ml of isopropanol. The mixture was boiled under reflux for 15 minutes and, after cooling, the NaCl which had precipitated was filtered off. The filtrate was concentrated in vacuo to about half its volume. A solution of 4.9 g (30 mmoles) of 3,4-methylenedioxyphenyl isocyanate in 30 ml of absolute dimethoxyethane was then added dropwise to this concentrated solution at −10° in the course of 25 minutes and the mixture was stirred for 20 minutes at −10° to 24° C., for 1 hour at 24° and for 1 hour at 40°-42° C. After cooling, the solid which had precipitated was filtered off and the filtrate was evaporated in vacuo at a bath temperature of 40°. The residue was taken up in 30 ml of ethyl acetate. Further (3,4-methylenedioxy-phenyl)-guanylurea crystallized out slowly from the solution. In total, 4.1 g (62% of theory) of this compound were obtained (m.p. charring above 250°). This product was suspended in 50 ml of dimethoxyethane and 25 ml of isopropanol, and 5.1 g (19 mmoles) of ethoxymethylenecyanoacetic acid 4-chloro-3-methyl-anilide were added. This mixture was stirred for 20 minutes at 23° C. and for 2.5 hours while boiling under reflux. After cooling, the solid was filtered off, washed with acetone and recrystallized from 2:1 dimethylformamide/acetonitrile. After drying, 2.10 g (26% based on 18.5 mmoles) of pure 4-amino-2-(3-(3,4-methylenedioxy-phenyl)-1-ureido)-pyrimidine-5-carboxylic acid 4-chloro-3-methyl-anilide of m.p. 276°-8° C. were then obtained.

Analysis: $C_{20}H_{17}ClN_6O_4$: found (%): C 54.0; H 3.8; Cl 8.0; N 18.7. calculated (%): C 54.5; H 3.9; Cl 8.0; N 19.1.

EXAMPLE 57

4-Amino-2-(3-(3,4-methylenedioxy-phenyl)-1-ureido)-pyrimidine-5-carboxylic acid 3-trifluoromethylanilide of m.p. 240°-2° C. was obtained by the procedure described in Example 56 (yield 19%).

Analysis: $C_{20}H_{15}F_3N_6O_4$: calculated (%): C 52.2; H 3.3; F 12.4; N 18.3, molecular weight 460.4. found (%): C 51.8; H 3.2; F 11.8; N 18.3, molecular weight 460.0 (by mass spectroscopy).

EXAMPLE 58

4-Amino-2-(3-octyl-1-ureido)-pyrimidine-5-carboxylic acid 3-chloro-2-methyl-anilide hydrochloride 0.81 ml of a 6.3 molar solution of HCl in ether was added to a suspension of 2.165 g (5 mmoles) of 4-amino-2-(3-octyl-1-ureido)-pyrimidine-5-carboxylic acid 3-chloro-2-methyl-anilide in 15 ml of absolute ethanol and the mixture was stirred for 1 hour at room temperature. The solid was then filtered off and washed with ethanol and ether. After drying, the hydrochloride thus obtained weighed 2.28 g and melted at 220°-2° C., solidified again and then melted at 323°-5° C.

Analysis: $C_{21}H_{30}Cl_2N_6O_2$: calculated (%): C 53.7; H 6.4; Cl 15.1; N 17.9. found (%): C 53.3; H 6.3; Cl 15.0; N 18.0 $Cl^{\ominus}$ 7.4.

EXAMPLE 59

4.0 g (42 mmoles) of guanidinium chloride were added to a solution of 0.92 g of sodium in 55 ml of isopropanol. The mixture was boiled under reflux for 15 minutes and the NaCl which had precipitated was filtered off at 10° C. A solution of 4 g (40 mmoles) of butyl isocyanate in 40 ml of dimethoxyethane was added dropwise to the filtrate at −10° C. in the course of 20 minutes and the mixture was stirred for a further 30 minutes at 0°, 30 minutes at room temperature and 1 hour at 40° C. A solution of 11.3 g (about 40 mmoles) of crude, oily ethoxymethylene-cyanoacetic acid N-ethyl-4-chloroanilide in 80 ml of dimethoxyethane was then added to the solution, which had been cooled to room temperature, and the resulting mixture was stirred for a further 40 minutes at room temperature and 3 hours while boiling under reflux. The reaction mixture was then evaporated in vacuo. The oily residue (18.4 g) was absorbed from 60 ml of $CH_2Cl_2$ on a 35 cm high ($\phi$=5.0 cm) silica gel S (0.063-0.2 mm, Riedel-DeHäen AG)/$CH_2Cl_2$ column and chromatographed. After elution with 800 ml of $CH_2Cl_2$, 300 ml of 100:2$CH_2Cl_2/C_2H_5OH$, 600 ml of 100: 3$CH_2Cl_2/C_2H_5OH$, 700 ml of 100: 4 $CH_2Cl_2/C_2H_5OH$ and 700 ml of 100: 5$CH_2Cl_2/C_2H_5OH$, 2.8 g of a by-product, which according to the IR spectrum contains a cyano group, were eluted with 600 ml of 100: 5$CH_2Cl_2/C_2H_5OH$ and 600 ml of 100: 6$CH_2Cl_2/C_2H_5OH$, and when elution was continued with 300 ml of 100: 7$CH_2Cl_2/C_2H_5OH$, 500 ml of 100: 8$CH_2Cl_2/C_2H_5OH$ and 500 ml of 100: 9$CH_2Cl_2/C_2H_5OH$, 1.80 g of a product in which the desired compound was indicated were eluted. After twice recrystallizing from methanol, this product gave 0.92 g (6%) of pure 4-amino-2-(3-butyl-1-ureido)-pyrimidine-5-carboxylic acid N-ethyl-4-chloro-anilide of m.p. 267°-9° C.

Analysis: $C_{18}H_{23}ClN_6O_2$: calculated (%): C 55.3; H 5.9; Cl 9.1; N 21.5, molecular weight 390.9. found (%): C 55.0; H 6.0; Cl 9.3; N 21.1, molecular weight 390; 392 (by mass spectroscopy).

EXAMPLE 60

3.30 g (2.83 ml, 31 mmoles) of N,N-dimethylcarbamyl chloride were added dropwise at 75° C. in the course of 20 minutes to a suspension of 5.95 g (20 mmoles) of 2,4-diamino-pyrimidine-5-carboxylic acid 3-trifluoromethyl-anilide and 2.05 g of triethylamine in 100 ml of acetonitrile and the mixture was stirred for a further 4 hours at 75° C. The suspended solid was separated off by filtering the warm reaction mixture, which was at 75°. On cooling to 5° C. (20 hours), crystalline product precipitated from the filtrate. This product was filtered off, washed with acetonitrile and dried. In this way, 2.2 g (30%) of pure 4-amino-2-(3,3-dimethyl-1-ureido)-pyrimidine-5-carboxylic acid 3-trifluoromethyl-anilide of m.p. 238°-40° C. were obtained (the melting point is very highly dependent on the heating rate; with normal heating the product gasifies at 236°-8° C. and crystallizes again; the above melting point was obtained by placing the sample at 210° C. in the melting point apparatus (Büchi SMP-20) and then heating at a rate of 2°/minute).

Analysis: $C_{15}H_{15}F_3N_6O_2$: calculated (%): C 48.9; H 4.1; F 15.5; N 22.8, molecular weight 368.3. found (%): C 48.6; H 4.1; F 15.5; N 22.8, molecular weight 368 (by mass spectroscopy).

EXAMPLE 61

Using 5.95 g (20 mmoles) of 2,4-diamino-pyrimidine-5-carboxylic acid 3-trifluoromethyl-anilide and 4.90 g (33 mmoles) of N,N-pentamethylene-carbamyl chloride (compare Boon, J. Chem. Soc. 1947, 313) as the starting materials, 1.55 g (19%) of pure 4-amino-2-(3,3-pentamethylene-1-ureido)-pyrimidine-5-carboxylic acid 3-trifluoromethyl-anilide of m.p. 228°-231° C. (decomposition) (same behavior at the decomposition temperature as the compound described in Example 60) were obtained by a procedure corresponding to that described in Example 60.

Analysis: $C_{18}H_{19}F_3N_6O_2$: calculated (%): C 52.9; H 4.7; F 14.0; N 20.6, molecular weight 408.4. found (%): C 52.6; H 4.6; F 13.6; N 20.4, molecular weight 408 (by mass spectroscopy).

EXAMPLE 62

Using 5.0 g (20 mmoles) of methoxymethylenecyanoacetic acid 3-chloro-4-methyl-anilide and 3.44 g (22 mmoles) of 1-amidino-4,4-dimethyl-imidazolidin-2-one as the starting materials, 6.83 g (91%) of pure 4-amino-2-(4,4-dimethyl-imidazolidin-2-on-1-yl)-pyrimidine-5-carboxylic acid 3-chloro-4-methyl-anilide of m.p. 290°–2° C. were obtained by the procedure described in Example 4. The product was identical (according to the IR spectrum and m.p.) to the compound obtained according to Example 4.

EXAMPLE 63

A solution of 0.285 g (12 mg atom) of sodium in 20 ml of absolute ethanol was added dropwise at 0° C. to a suspension of 3.42 g (12 mmoles) of 1-amidino-4-phenylimidazolidin-2-one hydrobromide in 25 ml of absolute ethanol, the mixture was stirred for 15 minutes at 23° C., a suspension of 3.80 g (13.3 mmoles) of ethoxymethylenecyanoacetic acid 3-trifluoromethyl-anilide in 25 ml of 1,2-dimethoxyethane was then added and the resulting mixture was stirred for 20 minutes at room temperature and for 2 hours while boiling under reflux. After cooling, the mixture was filtered and the filter residue was washed with water and ethanol. The filtrate was evaporated in vacuo and the residue which remained was mixed with ethyl acetate, whereupon further crystalline material was obtained, which was likewise isolated by filtering off. The two crystalline substances isolated (6.0 g together) were combined, a solution of 2 g of $NaHCO_3$ in 100 ml of water was added and the mixture was shaken for 4 hours. After filtering, the solid was washed with water and recrystallized from methanol. Together with a second crystalline product obtained after evaporating the mother liquor and again recrystallizing the resulting residue from methanol, 4.50 g (85%) of pure 4-amino-2-(4-phenyl-imidazolidin-2-on-1-yl)-pyrimidine-5-carboxylic acid 3-trifluoromethyl-anilide of m.p. 172°–4° C. were obtained in this way (after drying).

Analysis: $C_{21}H_{17}F_3N_6O_2$: calculated (%): C 57.0; H 3.9; F 12.9; N 19.0, molecular weight 442.4. found (%): C 56.8; H 4.1; F 12.5; N 18.7, molecular weight 442 (by mass spectroscopy).

EXAMPLES 64–74

The 4-amino-2-(imidazolidin-2-on-1-yl)-pyrimidine-5-carbanilides listed in Table 4 below were prepared in accordance with the procedure described in Example 4. The ethoxymethylene-cyanoacetanilides required as starting materials for the preparation of these compounds are listed in Table 5.

TABLE 4++

| Example No. | $R^7$ | $R^8$ | n | m.p. °C.** | Yield in % |
|---|---|---|---|---|---|
| 64 | 2-$CH_3$ | — | 0 | 265–6 | 87 |
| 65 | 4-$CF_3$ | — | 0 | 320–1 | 97 |
| 66 | 2-$CF_3$ | 4-Cl | 1 | 275–6 | 89 |
| 67 | 5-$CF_3$ | 2-F | 1 | 274–5 | 93 |
| 68 | 5-$CF_3$ | 2-Cl | 1 | 262–3 | 94 |
| 69 | 3-$CF_3$ | 4-Cl | 1 | 298–9 | 92 |
| 70 | 4-$OC_6H_5$ | 3-$CF_3$ | 1 | 240–1 | 97 |
| 71 | 4-$SC_6H_5$ | 3-$CF_3$ | 1 | 282–3 | 98 |
| 72 | 3-$CF_3$ | 5-$CF_3$ | 1 | 304–5 | 82 |
| 73 | 3-$CF_3$ | 4-$OCH_3$ | 1 | 301–2 | 95 |
| 74 | 4-O—⟨⟩—$OCH_3$ | 3-$CF_3$ | 1 | 263–4 | 82 |

++The compounds obtained according to Examples 64–74 gave the correct analytical values corresponding to the empirical formulae. In the IR spectrum, these compounds have a characteristic, intense band of the imidazolidinone carbonyl at 5.76–5.82 μ.

**In the majority of cases, the melting points are decomposition temperatures.

TABLE 5

Ethoxymethylene-cyanoacetanilides

| IIIA | $R^7$ | $R^8$ | m.p. °C. | Remarks |
|---|---|---|---|---|
| a | 2-$CF_3$ | — | 90–1 | E form |
| b | 4-$CF_3$ | — | 189–91 | E form |
| c | 2-$CF_3$ | 4-Cl | 107–8 | E/Z mixture |
| d | 5-$CF_3$ | 2-F | 167–8 | Z form |
| e | 5-$CF_3$ | 2-Cl | 165–6 | E/Z mixture |
| f | 3-$CF_3$ | 4-Cl | 187–8 | E form |
| g | 3-$CF_3$ | 5-$CF_3$ | 156–7 | E form |
| h | 4-$OC_6H_5$ | 3-$CF_3$ | 136–7 | E form |
| i | 4-$SC_6H_5$ | 3-$CF_3$ | 160–1 | E form |
| k | 3-$CF_3$ | 4-$OCH_3$ | 188–9 | E form |
| l | 4-O—⟨⟩—$OCH_3$ | 3-$CF_3$ | 151–2 | E form |

EXAMPLES 75–81

The 4-amino-2-(imidazolidin-2-on-1-yl)-pyrimidine-5-carbanilides listed in Table 6 below were prepared in accordance with the procedure described in Example 27. The ethoxymethylenecyanoacetanilides required as starting materials for the preparation of these compounds are listed in Table 5.

TABLE 6++

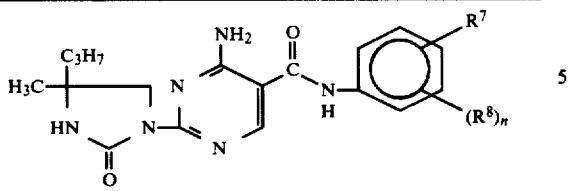

| Example No. | R⁷ | R⁸ | n | m.p. °C.** | Yield in % |
|---|---|---|---|---|---|
| 75 | 2-CF₃ | — | 0 | 258–9 | 86 |
| 76 | 4-CF₃ | — | 0 | 272–3 | 90 |
| 77 | 5-CF₃ | 2-F | 1 | 239–40 | 93 |
| 78 | 5-CF₃ | 2-Cl | 1 | 245–6 | 96 |
| 79 | 3-CF₃ | 4-Cl | 1 | 288–9 | 93 |
| 80 | 4-OC₆H₅ | 3-CF₃ | 1 | 256–7 | 86 |
| 81 | 4-SC₆H₅ | 3-CF₃ | 1 | | |

++The compounds obtained according to Examples 75-81 gave the correct analytical values corresponding to the empirical formulae. In the IR spectrum, these compounds have a characteristic intense band of the imidazolidinone carbonyl at 5.76–5.82 μ.
**In the majority of cases, the melting points are decomposition temperatures.

What is claimed is:

1. A 4-amino-2-ureido (or -thioureido)-pyrimidine-5-carboxylic acid anilide of the formula

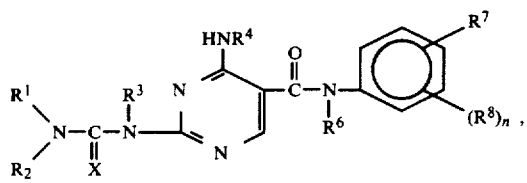

or a physiologically acceptable acid addition salt thereof, wherein

X is oxygen or sulfur, $R^1$ is hydrogen, $(C_1-C_3)$-alkyl, or phenyl;

$R^2$ taken alone is hydrogen, $(C_1-C_{10})$-alkyl, $(C_3-C_4)$-alkenyl, $(C_4-C_8)$-cycloalkyl, phenyl, phenylalkyl having 1 or 2 carbon atoms in the alkyl portion, or is phenyl or such phenylalkyl mono- or di-substituted in the benzene ring by $(C_1-C_3)$-alkyl, halogen, or $(C_1-C_4)$-alkoxy, or substituted by trifluoromethyl, methoxycarbonyl, ethoxycarbonyl, or methylenedioxy;

$R^3$ taken alone is hydrogen, $(C_1-C_3)$-alkyl, or phenyl;

$R^2$ and $R^3$ taken together are —(CH=CH)—, linear or branched $(C_2-C_8)$-alkylene, or such alkylene substituted by $(C_2-C_4)$-alkenyl, by phenyl, or by phenyl substituted by chlorine, bromine, methyl, ethyl, methoxy, or ethoxy;

$R^4$ is hydrogen or $(C_1-C_8)$-acyl;

$R^6$ is hydrogen, $(C_1-C_3)$-alkyl, $(C_3-C_4)$-alkenyl, benzyl, phenyl, benzyl mono- or di-substituted in the benzene ring by chlorine or methoxy, or phenyl substituted by methyl, chlorine, or by methyl and chlorine;

$R^7$ taken alone is hydrogen, $(C_1-C_3)$-alkyl, $(C_3-C_4)$-alkenyl, $(C_5-C_6)$-cycloalkyl, phenyl, halogen, trifluoromethyl, $(C_1-C_4)$-alkylthio, $(C_1-C_2)$-alkoxycarbonyl, cyano, acetamino, amino, nitro, carboxyl, $(C_1-C_4)$-alkoxy or

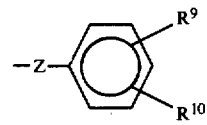

wherein

Z is oxygen, sulfur,

—CH₂—, or —CH₂CH₂—, and $R^9$ and $R^{10}$, which are the same or different, are hydrogen, fluorine, chlorine, bromine, $(C_1-C_3)$-alkyl, $(C_1-C_2)$-alkoxy, acetamino, $(C_1-C_2)$-alkoxycarbonyl, or carbonyl;

$R^8$ is fluorine, chlorine, bromine, methyl, $(C_1-C_2)$-alkoxy, or trifluoromethyl;

n is 0, 1, 2, or 3;

and if n is 1, then $R^7$ and $R^8$, taken together, may be methylenedioxy or ethylenedioxy.

2. A compound as in claim 1 which is 4-amino-2-(4,4-dimethyl-imidazolidin-2-on-1-yl)-pyrimidine-5-carboxylic acid 3-trifluoromethyl-anilide.

3. A compound as in claim 1 which is 4-amino-2-(4,4-dimethyl-imidazolidin-2-on-1-yl)-pyrimidine-5-carboxylic acid 3-chloro-2-methyl-anilide.

4. A compound as in claim 1 which is 4-amino-2-(4,4-dimethyl-imidazolidin-2-on-1-yl)-pyrimidine-5-carboxylic acid 2-fluoro-5-trifluoromethyl-anilide.

5. A compound as in claim 1 which is 4-amino-2-(4,4-dimethyl-imidazolidin-2-on-1-yl)-pyrimidine-5-carboxylic acid 2-chloro-5-trifluoromethyl-anilide.

6. A pharmaceutical composition for treating disturbances in the lipometabolism, said composition comprising an amount of a compound or salt as in claim 1 effective to affect the lipometabolism together with a pharmaceutically-acceptable carrier therefor.

7. A method for treating disturbances of the lipometabolism in a patient requiring such treatment, which method comprises administering to said patient an amount of a compound or salt as in claim 1 effective to affect the lipometabolism.

8. A pharmaceutical composition for treating adiposity, said composition comprising an amount, effective to induce anorexia, of a compound or salt as in claim 1 together with a pharmaceutically-acceptable carrier therefor.

9. A method for treating adiposity in a patient requiring such treatment, which method comprises administering to said patient an amount, effective to induce anorexia, of a compound or salt as in claim 1.

* * * * *